(12) United States Patent
Hareland et al.

(10) Patent No.: US 8,965,506 B2
(45) Date of Patent: Feb. 24, 2015

(54) FAULT TOLERANT PACING

(71) Applicant: Medtronic, Inc., Minneapolis, MN (US)

(72) Inventors: Scott A. Hareland, Lino Lakes, MN (US); Kenneth J Kahle, Cedar, MN (US); Leonard P Radtke, East Bethel, MN (US); John D. Wahlstrand, Shoreview, MN (US); Jeffrey M Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/706,430

(22) Filed: Dec. 6, 2012

(65) Prior Publication Data
US 2013/0165987 A1    Jun. 27, 2013

Related U.S. Application Data

(60) Provisional application No. 61/579,484, filed on Dec. 22, 2011.

(51) Int. Cl.
*A61N 1/37* (2006.01)
*A61N 1/08* (2006.01)
*A61B 5/0215* (2006.01)
*A61B 5/042* (2006.01)

(52) U.S. Cl.
CPC ............ *A61N 1/3706* (2013.01); *A61N 1/3702* (2013.01); *A61N 1/08* (2013.01); *A61B 2560/0276* (2013.01); *A61N 2001/083* (2013.01); *A61B 5/0215* (2013.01); *A61B 5/042* (2013.01)

USPC .................................. 607/27; 607/28; 607/29

(58) Field of Classification Search
CPC .............. A61N 1/08; A61N 2001/083; A61N 2001/36142; A61N 2001/37; A61N 2001/3702; A61N 2001/3706; A61N 2001/371; A61B 2560/0276
USPC ...................................................... 607/27–29
See application file for complete search history.

(56) References Cited

U.S. PATENT DOCUMENTS

| | | | | |
|---|---|---|---|---|
| 4,686,990 A * | 8/1987 | Moberg | ........................ | 607/29 |
| 5,800,460 A * | 9/1998 | Powers et al. | ..................... | 607/5 |
| 7,089,057 B2 * | 8/2006 | Heathershaw et al. | ......... | 607/27 |
| 8,170,682 B2 * | 5/2012 | Greenberg et al. | ............. | 607/63 |
| 8,195,294 B2 * | 6/2012 | Goetz et al. | ..................... | 607/27 |
| 8,355,783 B2 * | 1/2013 | Goetz et al. | ..................... | 607/27 |
| 2004/0162593 A1 * | 8/2004 | Jorgenson et al. | .............. | 607/27 |
| 2004/0260352 A1 * | 12/2004 | Rueter et al. | .................... | 607/28 |
| 2007/0270914 A1 * | 11/2007 | Vincent et al. | ................... | 607/27 |
| 2009/0299421 A1 * | 12/2009 | Sawchuk | .......................... | 607/4 |
| 2010/0198292 A1 * | 8/2010 | Honeck et al. | ................... | 607/17 |

* cited by examiner

*Primary Examiner* — Carl H Layno
*Assistant Examiner* — Eugene Wu
(74) *Attorney, Agent, or Firm* — Carol F. Barry

(57) ABSTRACT

Methods and/or devices may be configured to monitor the performance of pacing therapy and provide fault-tolerant operation to provide therapy in the event of certain failure modes occurring in the pacing delivery circuits, leads, and/or lead/tissue interfaces. Generally, the methods and/or devices may provide fault-detection, fault-recovery and fault-handling to, e.g., handle potential faults.

36 Claims, 13 Drawing Sheets

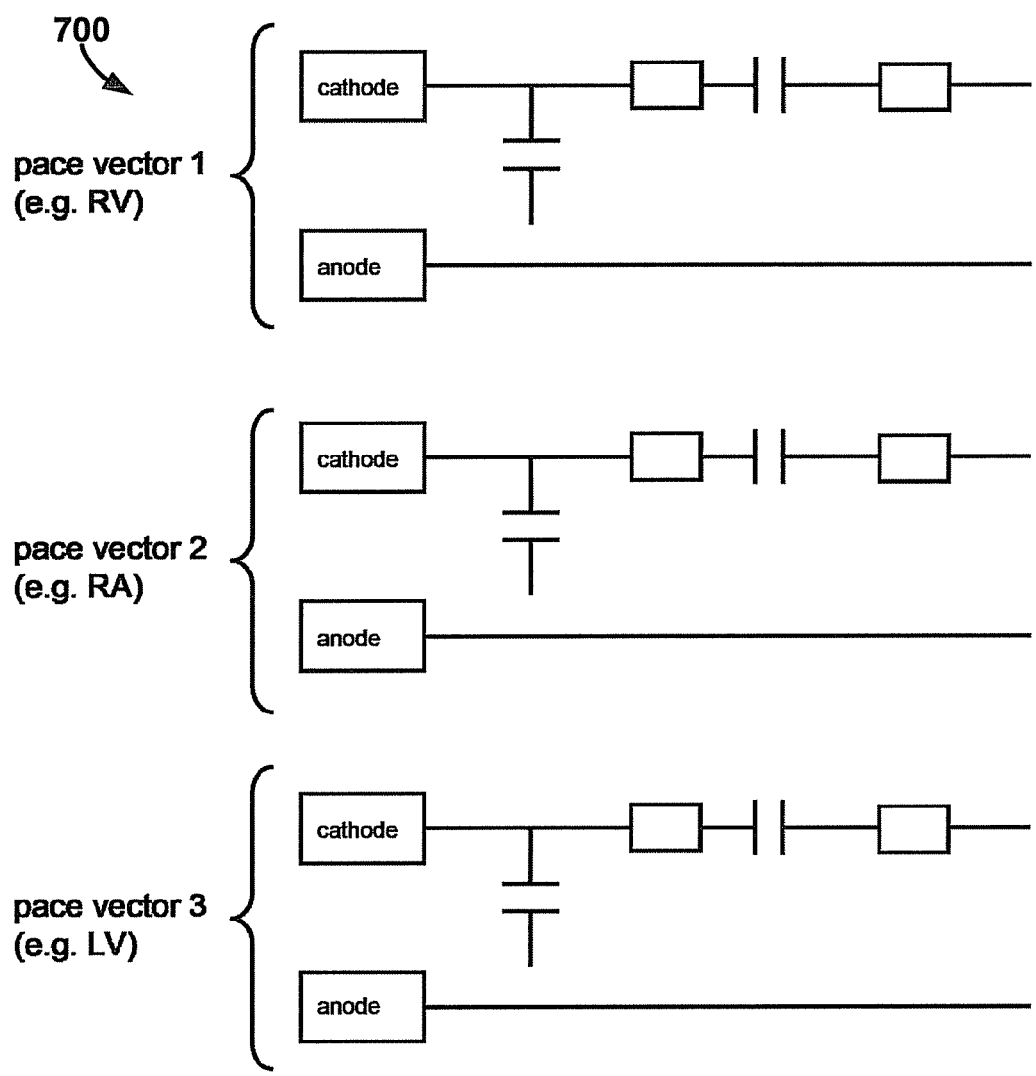

FAULT TOLERANT PACING

CROSS-REFERENCE TO RELATED APPLICATIONS

This application claims the benefit of U.S. Provisional Application No. 61/579,484, filed on Dec. 22, 2011. The disclosure of the above application is incorporated herein by reference in its entirety.

BACKGROUND OF THE INVENTION

The disclosure herein relates to determining and handling one or more faults associated with implantable medical devices delivering pacing therapy. More specifically, this disclosure describes methods for monitoring the performance of pacing therapy in an implantable medical device and methods to apply fault-tolerance to provide therapy in the event of certain failure modes occurring in the pacing delivery circuits, leads, and/or lead/tissue interfaces.

Implantable medical devices (IMD) are capable of utilizing pacing therapies to maintain hemodynamic benefits to patients. Pacing therapy may be delivered from an implantable generator, through a lead, and into the patient's heart. Basic programmable pacing parameters include pacing amplitude, pacing rate, pulse duration, and pacing pathway (e.g., bipolar such as a lead tip electrode to a lead ring electrode, etc. or unipolar such as a lead tip electrode to IMD casing, or housing), which all may be configured to ensure effective therapy to the patient.

Typically, modern pacing systems are designed and manufactured to mitigate any failures, or faults, such as, e.g., in the pacing output circuits (or generators) and/or the leads. In the rare event of such failures, or faults, the ability to continue to provide therapy using one or more techniques may be beneficial.

SUMMARY

This disclosure herein describes monitoring the performance of pacing therapy in an implantable medical device and providing fault-tolerant operation to provide therapy in the event of certain failure modes occurring in the pacing delivery circuits, leads, or lead/tissue interfaces. In other words, the disclosure herein relates to fault-detection, fault-recovery and fault-handling to, e.g., handle potential failure modes in a pacing system.

Exemplary fault-detection may include methods for determining, or assessing, one or more faults associated with an implantable medical device delivering pacing therapy, and the handling of such one or more faults. Such methods may include identifying at least one suspect parameter, e.g., lead impedance, delivered pacing capacitor energy, etc., of the implantable medical device indicative of a fault, and then sensing a physiological response of a patient during pacing therapy to determine whether a fault exists. Exemplary fault-recovery and fault-handling may include changing one or more parameters associated with the pacing therapy (e.g., voltage, pulse width, etc.), changing electrode vector configurations for the pacing therapy (e.g., according to a periodically-updated pacing reconfiguration table), and/or changing pacing output circuit configurations for the pacing therapy, and further may include determining whether any of the changes were successful.

Further, the ability of exemplary devices and/or system to reconfigure the pacing therapy delivery vector and waveform under certain failure scenarios may be beneficial to provide life sustaining therapy. The ability to detect, recover from, and handle potential faults in basic pacing therapy may mitigate several failure modes.

One exemplary embodiment of an implantable medical device for use in delivering pacing therapy to a patient may include a therapy delivery module configured to deliver pacing therapy to a patient, sensing apparatus configured to monitor at least one physiological response of the patient in response to the delivery of pacing therapy, and a control module coupled to the therapy delivery module and to the sensing apparatus. The control module may be further configured to initiate the delivery of pacing therapy to the patient and monitor one or more parameters of the implantable medical device during the delivery of pacing therapy (e.g., monitoring at least one of delivered pacing capacitor energy and lead impedance, conducting built-in self-tests, etc.). The control module may be further configured to identify at least one suspect parameter in the one or more monitored parameters indicative of one or more faults associated with the implantable medical device that require action to be taken for handling of the one or more faults, sense (e.g., using the sensing apparatus) at least one physiological response of the patient during the delivery of pacing therapy (e.g., over a selected number of heart beats) in response to identifying the at least one suspect parameter prior to initiating action to handle the one or more indicated faults, and determine whether a fault exists based on the at least one physiological response sensed during the delivery of pacing therapy (e.g., over the selected number of heart beats).

One exemplary fault detection method for use in detecting one or more faults associated with an implantable medical device that require action to be taken for handling of the one or more faults may include delivering pacing therapy to a patient using an implantable medical device, monitoring one or more parameters of the implantable medical device during the delivery of pacing therapy (e.g., monitoring at least one of delivered pacing capacitor energy and lead impedance, conducting built-in self-tests, etc.), and identifying at least one suspect parameter in the one or more monitored parameters indicative of one or more faults associated with the implantable medical device that require action to be taken for handling of the one or more faults. The exemplary method may further include sensing at least one physiological response of the patient during the delivery of pacing therapy (e.g., over a selected number of heart beats) in response to identifying the at least one suspect parameter prior to initiating action to handle the one or more indicated faults and determining whether a fault exists based on the at least one physiological response sensed during delivery of pacing therapy (e.g., over the selected number of heart beats).

In one or more embodiments of the devices and methods described herein, determining whether a fault exists based on the at least one physiological response sensed during the delivery of pacing therapy may include determining whether the at least one sensed physiological response is an expected physiological response to the delivery of pacing therapy.

In one or more embodiments of the devices and methods described herein, the control module may be further configured to execute and the method may further include performing diagnostics of internal pacing circuitry and one or more leads of the implantable medical device to determine if the detected fault is associated with one of the internal pacing circuitry and the one or more leads in response to determining that a fault exists.

In one or more embodiments of the devices and methods described herein, the control module may be further configured to execute and the method may further include modifying the pacing therapy by changing at least one parameter of the pacing therapy in response to determining that a fault exists (e.g., changing the pacing therapy to a maximum output for the pacing therapy using the implantable medical device), sensing at least one physiological response of the patient during delivery of the modified pacing therapy, and performing fault handling operations if the at least one sensed physiological response of the patient during delivery of the modified pacing therapy is not an expected physiological response to the delivery of the modified pacing therapy.

In one or more embodiments of the devices and methods described herein, the control module may be further configured to execute and the method may further include periodically sensing at a periodic sensing rate at least one physiological response of the patient during the delivery of pacing therapy for use in determining whether a fault exists. Sensing at least one physiological response of the patient during delivery of pacing therapy in response to identifying the at least one suspect parameter may interrupt the periodic sensing at the periodic sensing rate.

In one or more embodiments of the devices and methods described herein, identifying at least one suspect parameter in the one or more monitored parameters indicative of one or more faults includes at least one of monitoring/analyzing clock speed (e.g., comparing to a reference clock), testing a power supply, testing internal pacing circuitry, etc. In one or more embodiments of the devices and methods described herein, to handle a determined fault, the control module may be configured to execute and the method may further include reconfiguring at least one of an electrode vector configuration and pacing output circuit configuration for the pacing therapy in response to determining that a fault exists.

One exemplary implantable medical device for use in delivering pacing therapy to a patient may include a housing, a first electrode (e.g., configured to deliver pacing therapy to the patient's right ventricle) and a second electrode, a first pacing output circuit located within the housing, a second pacing output circuit located within the housing, and a control module coupled to the first pacing output circuit and the second pacing output circuit. The first pacing output circuit may be configured to deliver pacing therapy to the patient using the first electrode, and the second pacing output circuit may be configured to deliver pacing therapy to the patient using the second electrode. The control module may be configured to determine if a fault exists in the first pacing output circuit (e.g., test the first pacing output circuit) and to reconfigure the second pacing output circuit to deliver pacing therapy using the first electrode if a fault is determined to exist in the first pacing output circuit.

One exemplary fault handling method for use in an implantable medical device may include delivering pacing therapy to a patient using an implantable medical device, determining if a fault exists in a first pacing output circuit configured to deliver pacing therapy to the patient (e.g., to patient's right ventricle) using a first electrode (e.g., testing the first pacing output circuit), and reconfiguring a second pacing output circuit to deliver pacing therapy using a first electrode if a fault is determined to exist in the first pacing output circuit.

In one or more embodiments described herein, the control module may be further configured to execute and the method may further include delivering pacing therapy with the first electrode using the second pacing output circuit during a first time period and delivering pacing therapy with the second electrode using the second pacing output circuit during a second time period where the first time period and the second time period do not overlap. Further, the control module may be further configured to execute and the method may further include setting the voltage of the pacing therapy delivered by the second pacing output circuit to the higher of the voltage of the pacing therapy delivered with the first electrode using the first pacing output circuit and the voltage of the pacing therapy delivered with the second electrode using the second pacing output circuit.

In one or more embodiments described herein, the control module may be further configured to execute and the method may further include reconfiguring a third pacing output circuit to deliver pacing therapy with at least one of the second electrode and a third electrode if a fault is determined to exist in the first pacing output circuit. Further, the control module may be further configured to execute and the method may further include delivering pacing therapy with the second electrode using the third pacing circuit during a first time period and delivering pacing therapy with the third electrode using the third pacing circuit during a second time period where the first time period and the second time period do not overlap.

In one or more embodiments described herein, the control module may be further configured to execute and the method may further include reconfiguring the first pacing output circuit to deliver pacing therapy with the second electrode if no fault is determined to exist in the first pacing output circuit.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIGS. 11A-C are diagrams of exemplary methods of fault handling using pacing output circuit reconfiguration.

DETAILED DESCRIPTION OF EXEMPLARY EMBODIMENTS

Figure 1:
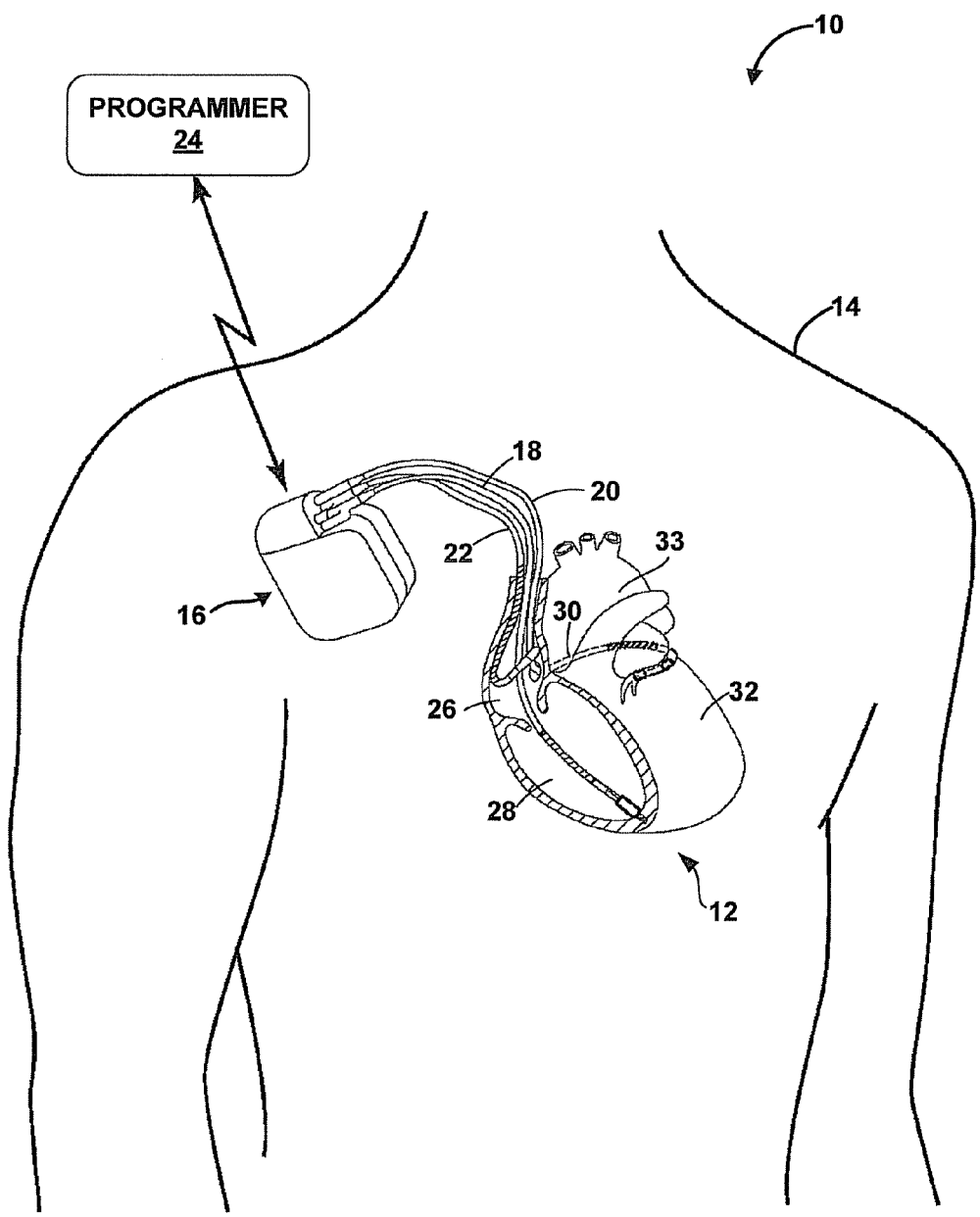
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-11. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
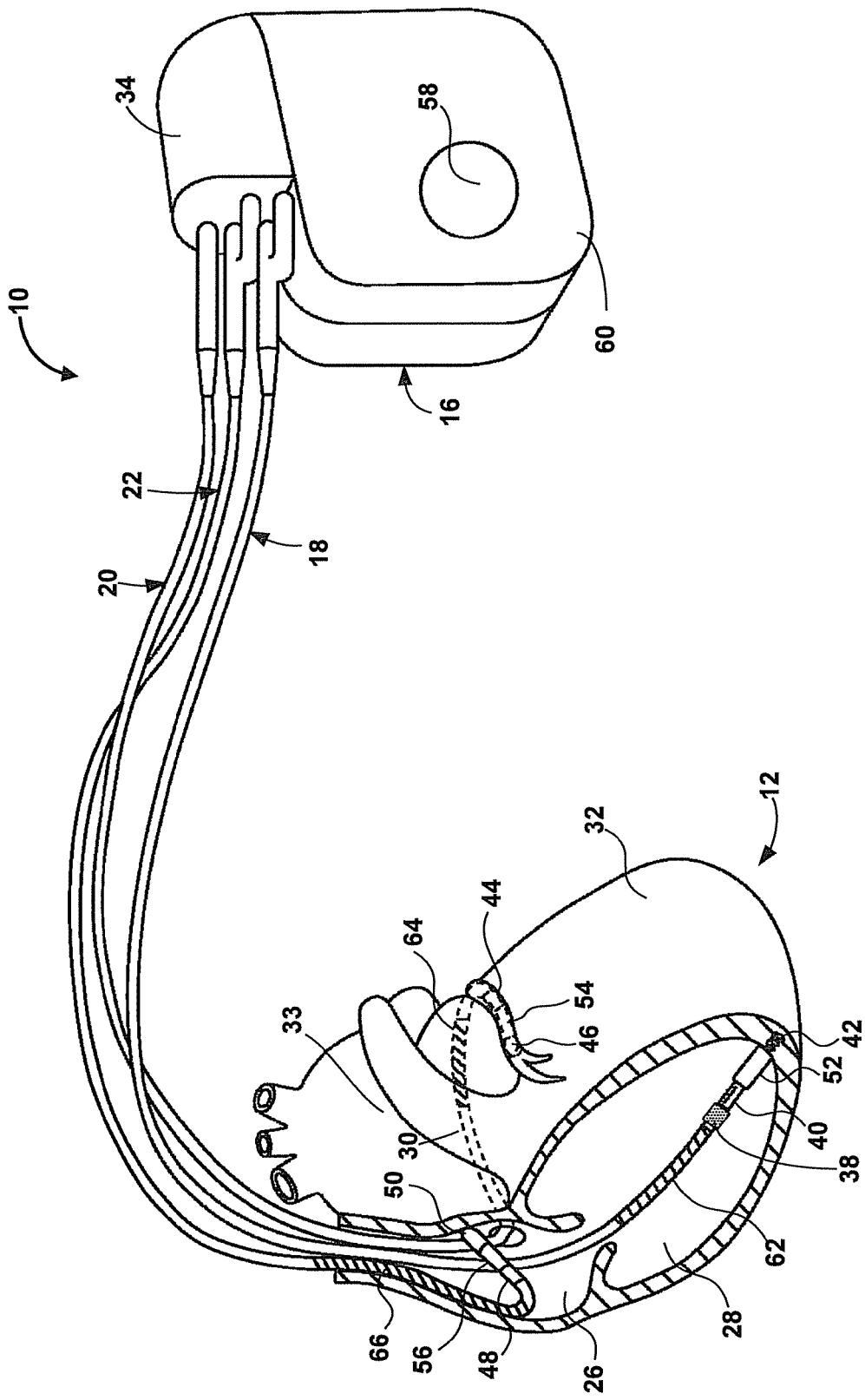
FIG. 2 is a diagram of the exemplary IMD of FIG. 1 including 3 leads.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., to monitor one or more physiological parameters of the patient 14 during pacing therapy so as to sense at least one physiological response), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22. As shown in FIG. 2, the pressure sensor 38 is disposed in the right ventricle 28 of the patient's heart 12. The pressure sensor 38 may respond to an absolute pressure inside the right ventricle 28, and may be, e.g., a capacitive and/or piezoelectric pressure sensor. In other examples, the pressure sensor 38 may be positioned within other regions of the heart 12 (e.g., the left ventricle) and may monitor pressure within one or more of the other regions of the heart 12, or may be positioned elsewhere within or proximate to the cardiovascular system of the patient 14 to monitor cardiovascular pressure associated with mechanical contraction of the heart.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the coiled conductors within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48 and 50 may be used for unipolar sensing or pacing in combination with housing electrode 58. As described in further detail with reference to FIG. 4, the housing 60 may enclose a therapy delivery module that may include a stimulation generator for generating cardiac pacing pulses and defibrillation or cardioversion shocks, as well as a sensing module for monitoring the patient's heart rhythm.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes.

The pressure sensor 38 may be coupled to one or more coiled conductors within the lead 18. In FIG. 2, the pressure sensor 38 is located more distally on the lead 18 than the elongated electrode 62. In other examples, the pressure sensor 38 may be positioned more proximally than the elongated electrode 62, rather than distal to the electrode 62. Further, the pressure sensor 38 may be coupled to another one of the leads 20, 22 in other examples, or to a lead other than the leads 18, 20, 22 carrying stimulation and sense electrodes. In addition, for example, the pressure sensor 38 may be self-contained device that is implanted within the heart 12, such as within the septum separating the right ventricle 28 from the left ventricle 32, or the septum separating the right atrium 26 from the left atrium 33. In such an example, the pressure sensor 38 may wirelessly communicate with a sensing module of the IMD 16.

The configuration of the therapy system 10 illustrated in FIGS. 1-2 is merely one example. In other examples, a therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12.

In other examples of therapy systems that provide electrical stimulation therapy to the heart 12, a therapy system may include any suitable number of leads coupled to the IMD 16, and each of the leads may extend to any location within or proximate to the heart 12. For example, other examples of therapy systems may include three transvenous leads located as illustrated in FIGS. 1-2, and an additional lead located within or proximate to the left atrium 33. Still further, other therapy systems may include a single lead that extends from the IMD 16 into the right atrium 26 or the right ventricle 28, or two leads that extend into a respective one of the right atrium 26 and the right ventricle 28. An example of this type of therapy system is shown in FIG. 3.

Figure 3:
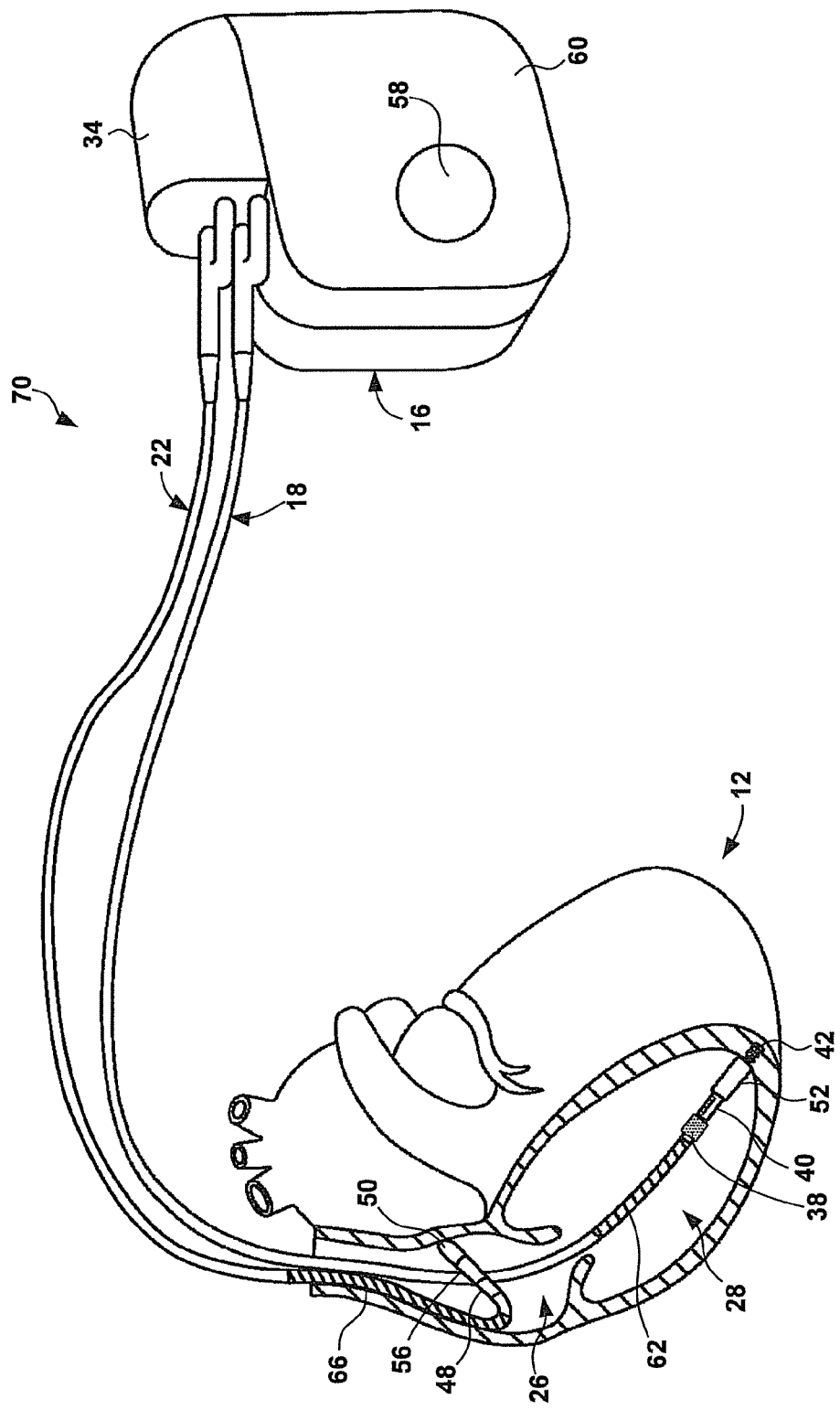
FIG. 3 is a diagram of another exemplary IMD of FIG. 1 including 2 leads.

FIG. 3 is a conceptual diagram illustrating another example of a therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing pacing therapy (e.g., pacing pulses) and defibrillation to a patient's heart 12.

Figure 4:
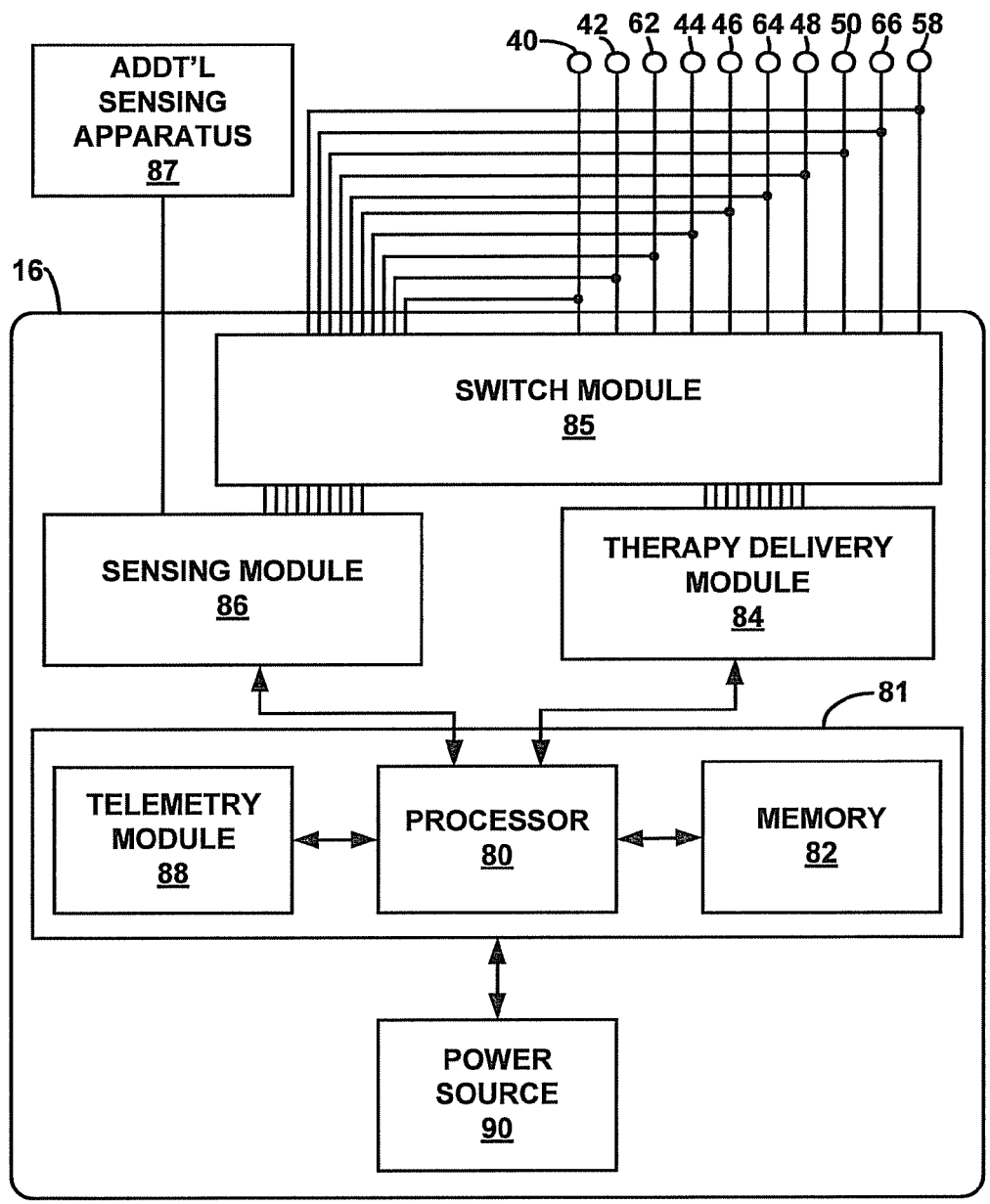
FIG. 4 is a block diagram of an exemplary IMD, e.g., the IMD of FIGS. 1-3.

FIG. 4 is a functional block diagram of one example configuration of IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 controls the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy deliver module 84 to deliver electrical pulses with the amplitudes, pulse widths, frequency, or electrode polarities specified by the selected one or more therapy programs (e.g., pacing therapy programs, pacing recovery programs, fault recovery programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing pulses via ring electrodes 40, 44, 48 coupled to leads 18, 20, and 22, respectively, and/or helical electrodes 42, 46, and 50 of leads 18, 20, and 22, respectively. Further, for example, therapy delivery module 84 may deliver defibrillation shocks to heart 12 via at least two electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrode for delivery of therapy to a pacing vector). In other words, each electrode can be selectively coupled to one of the pacing output circuits of the therapy delivery module using the switching module 85. The control module 81 may configure the switch module 85 such that a single pacing output circuit provides pacing therapy (e.g., electrical pulses) to more than one electrode at different times or at the same time.

The sensing module 86 is coupled (e.g., electrically coupled) to sensing apparatus, which may include, among other sensing apparatus, the electrodes 40, 42, 44, 46, 48, 50, 58, 62, 64, 66 to monitor electrical activity of the heart 12, e.g., impedance signals between two or more electrodes (e.g., right and/or left ventricle impedance, subcutaneous impedance, impedance waveform during ejection, impedance waveform during filling, etc.), electrocardiogram (ECG) signals, etc. The impedance signals may be used to monitor stroke volume (SV), ejection time (ET), etc. The ECG signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc. The sensing module 86 may be further coupled (e.g., electrically coupled) to additional sensing apparatus 87, which may further include one or more pressure sensors, posture sensors (e.g., 2-D and/or 3-D accelerometers), heart sound sensors, activity sensors, perfusion sensors, etc. to monitor one or more heart-related physiological parameters such as, e.g., patient posture, ejection time, stroke volume, cardiac output, pre-ejection time, filling time, normalized ejection time % (ejection time divided by the R-R interval expressed as a percentage), etc.

The switch module 85 may be also be used with the sensing module 85 to select which of the available electrodes are used to, e.g., sense heart activity. In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to detect and classify the patient's heart rhythm from the electrical signals. For example, the processor 80 may detect and classify the heart rhythm of patient 14 by employing any of the numerous signal processing methodologies known in the art.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, WI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pace timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

The value of the count present in the escape interval counters when reset by sensed R-waves and P-waves may be used the control module 81 (e.g., the processor 80) to measure the durations of R-R intervals, P-P intervals, P-R intervals and R-P intervals, which are measurements that may be stored in memory 82. The controller or control module 81 may use the count in the interval counters to detect a tachyarrhythmia event, such as ventricular fibrillation event or ventricular tachycardia event. Upon detecting a threshold number of tachyarrhythmia events, the control module 81 may identify the presence of a tachyarrhythmia episode, such as a ventricular fibrillation episode, a ventricular tachycardia episode, or a non-sustained tachycardia (NST) episode.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

In the examples described herein, the control module 81 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82. In addition, the number of tachyarrhythmia events that are detected to confirm the presence of a tachyarrhythmia episode may be stored as a number of intervals to detect (NID) threshold value in memory 82. In some examples, the control module 81 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, the control module 81 may determine that the tachyarrhythmia is present.

If the control module 81 detects an atrial or ventricular tachyarrhythmia based on signals from sensing module 86, and an anti-tachyarrhythmia pacing regimen is desired, timing intervals for controlling the generation of anti-tachyarrhythmia pacing therapies by therapy delivery module 84 may be loaded into the pacer timing and control module to control the operation of the escape interval counters therein and to define refractory periods during which detection of R-waves and P-waves is ineffective to restart the escape interval counters.

If IMD 16 is configured to generate and deliver defibrillation shocks to the heart 12, the therapy delivery module 84 may include a high voltage charge circuit and a high voltage output circuit. In the event that generation of a cardioversion or defibrillation shock is required, the control module 81 may employ the escape interval counter to control timing of such cardioversion and defibrillation shocks, as well as associated refractory periods. In response to the detection of atrial or ventricular fibrillation or tachyarrhythmia requiring a cardioversion pulse, the control module 81 may activate a cardioversion/defibrillation module, which may, like pacer timing and control module, be a hardware component of the control module 81 and/or a firmware or software module executed by one or more hardware components of the processor 80. The cardioversion/defibrillation control module may initiate charging of the high voltage capacitors of the high voltage charge circuit of therapy delivery 84 under control of a high voltage charging control line.

The control module 81 may monitor the voltage on the high voltage capacitor, e.g., via a voltage charging and potential (VCAP) line. In response to the voltage on the high voltage capacitor reaching a predetermined value set by the control module 81, the control module 81 may generate a logic signal that terminates charging. Thereafter, timing of the delivery of the defibrillation or cardioversion pulse by therapy delivery 84 may be controlled by the cardioversion/defibrillation module. Following delivery of the fibrillation or tachycardia therapy, the control module 81 may return the therapy delivery module 84 to a cardiac pacing function and await the next successive interrupt due to pacing or the occurrence of a sensed atrial or ventricular depolarization.

The therapy delivery module 84 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by, e.g., the switch module 85.

The telemetry module 88 of the control module 81 may include any suitable hardware, firmware, software, or any combination thereof for communicating with another device, such as the programmer 24 (FIG. 1). For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

The exemplary methods and/or devices described herein may utilize a fault-detection scheme as well as fault-recovery and fault-handling stages to bypass potential failure modes in the system. One manifestation of the basic flow can be seen in exemplary method 100 of FIG. 5, which illustrates a flowchart/activity diagram for the various stages. Exemplary method 100 includes various processes to detect and handle faults associated with an IMD, such as IMD 16, during the delivery of pacing therapy. Exemplary method 100 is intended to illustrate the general functional operation of the devices described herein, and should not be construed as reflective of a specific form of software or hardware necessary to practice all of the methods described herein. It is believed that the particular form of software will be determined primarily by the particular system architecture employed in the device (e.g., IMD 16) and by the particular detection and therapy delivery methodologies employed by the device and/or system. Providing software and/or hardware to accomplish the described methods in the context of any modern IMD, given the disclosure herein, is within the abilities of one of skill in the art.

Figure 5:
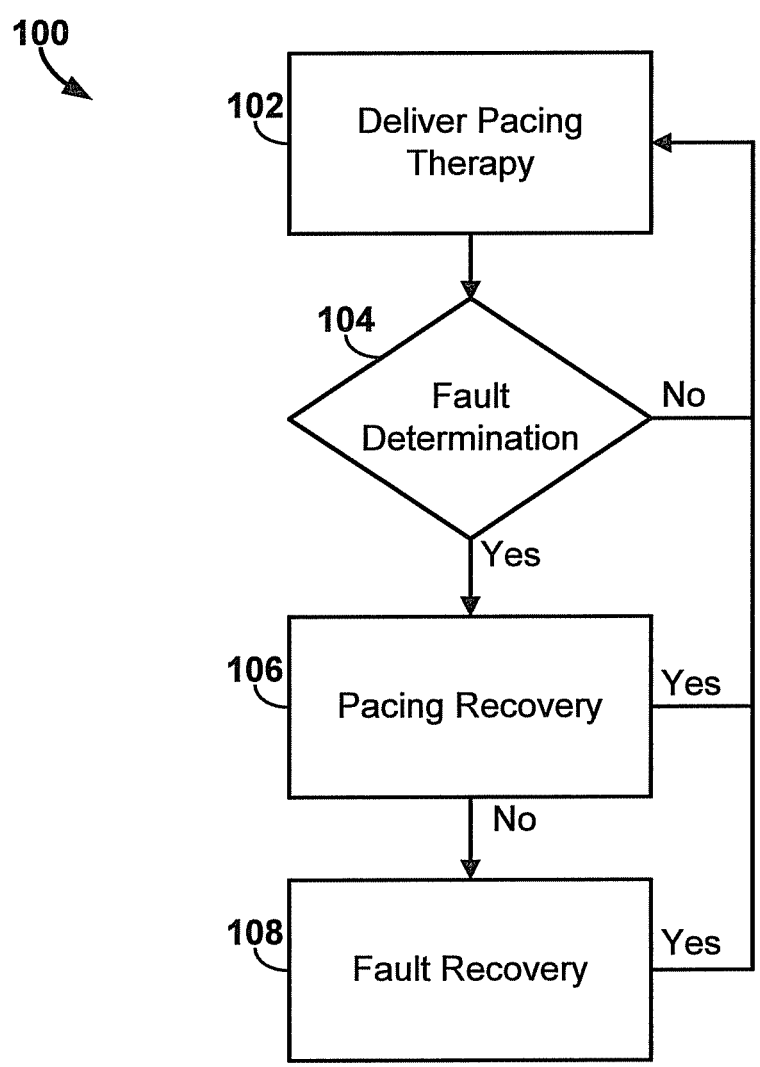
FIG. 5 is a general flow chart of an exemplary method for use in a fault tolerant pacing system, e.g., using the IMDs of FIGS. 1-4.

The exemplary method 100 of FIG. 5 includes delivering pacing therapy 102 (e.g., using the IMD 16 described herein). Delivering pacing therapy 102 may include monitoring a patient's heart and delivering electrical pacing pulses to the patient's heart, e.g., to maintain the patient's heart beat (e.g., to regulate a patient's heart beat).

During the delivery of pacing therapy 102, one or more faults associated with the delivery of pacing therapy, e.g., using an IMD, may be detected or determined 104. Exemplary methods and/or processes that may be used to detect, or determine, one or more faults associated with the device delivering pacing therapy are further described herein with reference to FIGS. 6-7. If no faults are detected 104, the exemplary method may continue to deliver pacing therapy 102.

If a fault is detected 104, the exemplary method 100 may proceed to pacing recovery 106, e.g., to attempt to recapture the patient's heart using modified pacing parameters to maintain an acceptable level of cardiac activity. For example, pacing recovery 106 may include modifying one or more parameters associated with the pacing therapy such as, e.g., voltage, pulse width, etc. and/or applying one or more capture management processes. An exemplary method that may be used for pacing recovery is further described herein with reference to FIG. 8. If pacing recovery occurs (e.g., the pacing at modified parameters is successful as indicated by sensed parameters as having suitable capture of the patient's heart), the exemplary method may return to delivering pacing therapy 102 (e.g., with modified pacing parameters, etc.).

If the pacing recovery does not occur, the exemplary method 100 may proceed to fault recovery 108. Fault recovery 108 may include one or more methods and/or processes used to recover from one or more detected faults. Exemplary methods and/or processes that may be used for fault recovery are further described herein with reference to FIGS. 9-12. If the exemplary method 100 recovers from the one or more detected faults, the method 100 may return to delivering pacing therapy 102. If the exemplary method 100 does not recover from the one or more faults, the method 100 may, e.g., alert the patient and/or a clinician (e.g., using telemetry).

During normal pacing therapy, an exemplary IMD or system can be configured to both sense and pace, or simply just pace without sensing. Detection of faults (e.g., errors, failures, etc.) associated with the pacing therapy may be beneficial for pacing therapy. Detection involves ensuring that an intended pace signal indeed translates into a physiological response by a patient. This detection may be achieved in several ways including, e.g., real-time sensing of one or more physiological responses to the delivery of pacing therapy and/or real-time measurement of pacing capacitor energy delivered.

Depending upon the patient and their dependency on pacing therapy, these sensing features can be implemented in real-time (e.g., beat-to-beat basis) or on a less frequent basis (e.g., one out of every ten pulses, once every minute, etc.). For example, the detection may occur on every pacing pulse in order to maintain maximum pacing efficacy detection. As long as the appropriate physiological pacing response is seen, an exemplary pacing device and/or system can continue to operate under normal pacing therapy.

Sensing of a physiological response to the delivery of pacing therapy is often not electrically efficient. In other words, the sensing of a physiological response to the delivery of pacing therapy often consumes an excessive amount of electrical power. In IMDs, which may be intended to be implanted for an extended time period, improving electrical efficiency is advantageous. Sensing a physiological response to the delivery of pacing therapy for every beat may be avoided using the exemplary method described herein with reference to FIG. 6, e.g., thereby saving electrical energy, or in other words, improving electrical efficiency, but still allowing faults in the system to be detected.

Figure 6:
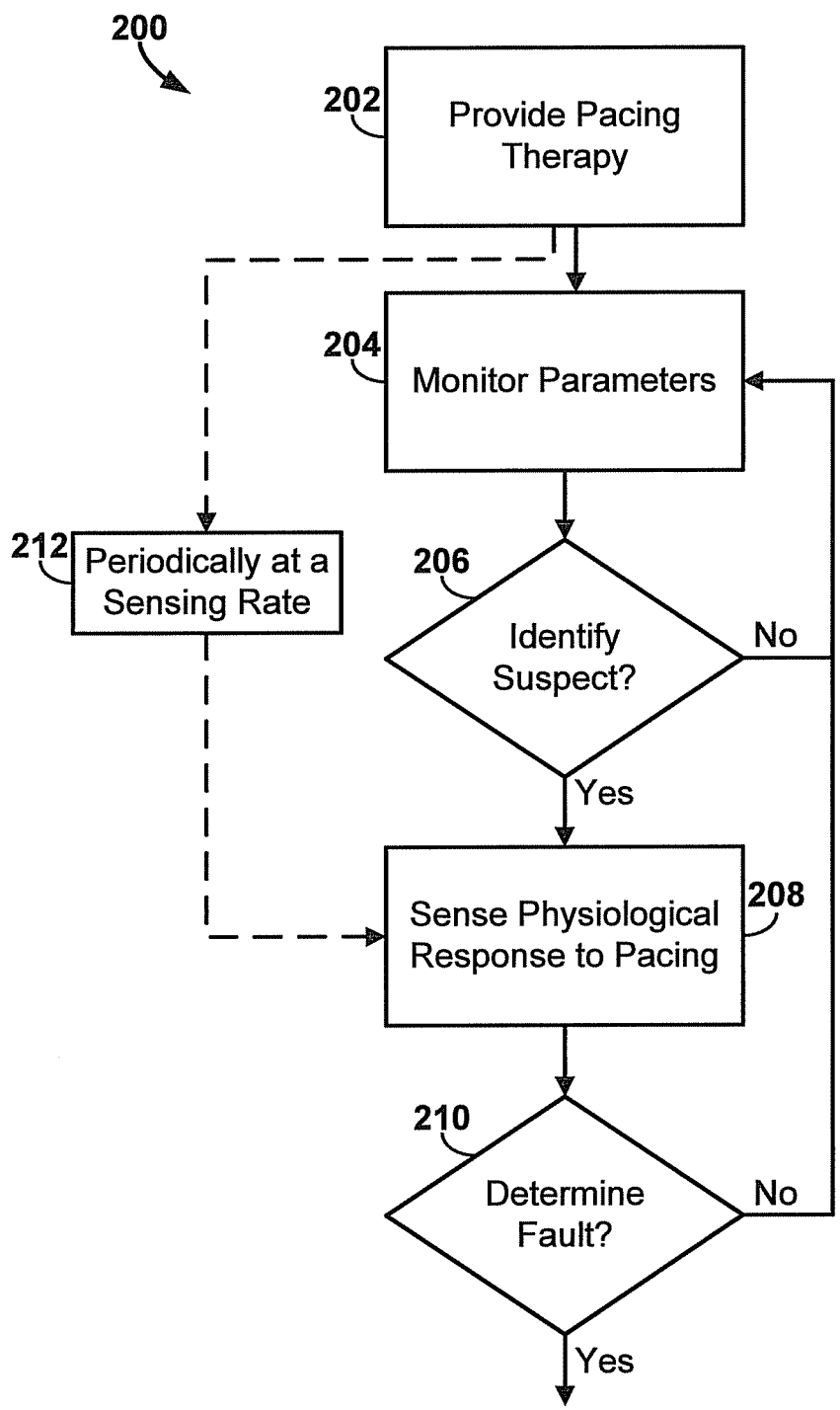
FIG. 6 is a flow chart of an exemplary method of fault determination from FIG. 5.

An exemplary method 200 of fault detection is depicted in FIG. 6. The exemplary method 200 may include providing pacing therapy 202, e.g., to regulate a patient's heart using an IMD such as the IMD 16 described herein with reference to FIGS. 1-4. During the delivery of pacing therapy, one or more parameters that may be indicative of one or more faults associated with the device providing therapy may be monitored 204.

For example, delivered pacing capacitor energy may be monitored 204. The delivered pacing capacitor energy may include the energy delivered for each pacing pulse of the pacing therapy. For instance, each pacing output circuit, e.g., of the therapy delivery module 84 of the IMD 16, may include a capacitor that is charged prior to each pacing pulse. By measuring the voltage of the capacitor before and after each pacing pulse, a change in voltage may be determined. A decrease, or an increase, in the change in voltage may be indicative of a fault associated with the device delivering the pacing therapy (e.g., IMD 16). For example, if the change in voltage is too small, not enough energy being delivered may be indicated, if the change in voltage is too large, a leakage path may exist, etc.

In other words, measurement of pacing capacitor energy may include measuring, or monitoring, a change in voltage (e.g., change in voltage=initial voltage before pacing pulse minus final voltage after pacing pulse) of a pacing capacitor in a pacing output circuit such as found in the therapy delivery module 84 of IMD 16 described herein with reference to FIG. 4.

Further, for example, the lead impedance may be monitored 204. Monitoring the lead impedance may include monitoring the impedance of each circuit located in each lead electrically coupling one or more pacing output circuits to one or more electrodes located on each lead. In other words, the impedance of each circuit located in each lead may be monitored. An exemplary method for monitoring lead impedance may be described in U.S. Pat. No. 5,201,865 entitled "Medical Lead Impedance Measurement System" to Kevin, P. Kuehn and issued on Apr. 13, 1993, which is hereby incorporated by reference in its entirety. Changes in lead impedance may be indicative of a fault located in the lead, that a lead has become dislodged, etc.

Still further, for example, monitoring one or parameters indicative of one or more faults 204 may include a built-in self-test (BIST). The BIST may include testing one or more circuits inside of the pacing system and/or device except for the circuits and conductors located within the leads. In other words, the BIST may be internal to, e.g., the housing 60 of the IMD 16. The BIST may include tests that monitor/analyze clock speed, e.g., within the control module 81 (e.g., compare the clock to a reference clock), test power supplies, e.g., such as power source 90, test one or more pacing output circuits, e.g., of the therapy delivery module 84, etc. The BIST may further include leakage detection tests on discrete capacitors (e.g., charging a capacitor and monitoring the voltage across the capacitor over time to determine if the capacitor is leaking current), charge pump efficiency tests (e.g., charging a capacitor using a charge pump and monitor the amount of time, or clock cycles, it takes to charge the capacitor), capacitor voltage charge tests (e.g., monitoring the amount of energy required to charge a capacitor), digital logic circuitry tests, analog-to-digital convertor tests, etc.

The exemplary method 200 may further analyze the one or more monitored parameters to identify one or more (e.g., at least one) suspect parameters 206, or exceptions, that may be indicative of one or more faults associated within the pacing system and/or device (e.g., IMD 16) that may require action to be taken for handling of the one or more faults. In other words, this identification process 206 is a precursor to any action being taken to handle any possible faults. As described herein, the delivered pacing capacitor energy, lead impedance, BIST, and/or any other monitored parameter may be useful in the detection, or indication, of faults, and may be analyzed to identify a suspect parameter indicative of one or more faults.

For example, as described herein, if the delivered pacing capacitor energy and/or lead impedance is not what is expected (e.g., too high, too low, etc.), it may be identified, or labeled, as suspect. In at least one embodiment, each monitored parameter may be compared to a selected value indicative of normal operation. In at least another embodiment, a running average of a monitored parameter over a selected number of beats may be used to determine if it is suspect. Any statistical or mathematical process may be used to analyze the one or more monitored parameters for indication of one or more faults.

If no monitored parameters are identified as being suspect, the exemplary method 200 may continue providing pacing therapy 202 and monitoring parameters 204. Although the monitoring parameters process 204 and the identifying suspect parameters process 206 are shown as being consecutive, they may also occur simultaneously (e.g., as the parameters are being monitored, they may also be analyzed for identification of suspect parameters).

If at least one monitored parameter is identified as being suspect, the exemplary method 200 may proceed to sensing at least one physiological response of the patient during the delivery of pacing therapy 208 prior to initiating any one or more actions to handle any potential faults. For example, one or more physiological parameters of the patient's heart may be monitored to determine whether the pacing therapy is successfully triggering heart beats. More specifically, an intrinsic heart beat (e.g., natural sinus rhythm) and an evoked, or paced, heart beat may appear differently on an electrogram, and thus, the exemplary methods and devices described herein may utilize various signal processing techniques to analyze the monitored electrical activity of the patient's heart and to determine whether the pacing therapy is successfully triggering heart beats (e.g., as opposed to intrinsic conductions). Further, in at least one embodiment, the ejection time of a patient's heart may be monitored (e.g., using one or more pressure sensors, etc.) to determine whether the pacing therapy is successfully triggering heart beats.

The exemplary method 200 may determine if a fault exists 210 based on the monitored physiological response 208. For example, if the monitored physiological response 208 is not what is expected in response to the pacing therapy (e.g., outside a range of expected behavior, etc.), the method 200 may determine that a fault exists. If a fault is not determined to exist, the method 200 may continue, or return to, providing pacing therapy 202 and monitoring one or more parameters 204 associated with the IMD delivering pacing therapy.

In systems and/or devices that may contain one or more faults, a physiological response (e.g., a desired physiological response) to pacing therapy may be inconsistent. For example, the physiological response to pacing therapy may occur most of the time and be absent some of the time. In these situations, a physiological response may be analyzed over a period of time to determine if a fault exists (e.g., over a selected number of heart beats).

In one or more embodiments, the physiological response may be monitored over a selected number of heart beats such as, e.g., less than or equal to about 3 heart beats, about 5 heart beats, about 8 heart beats, about 10 heart beats, about 12 heart beats, about 20 heart beats, about 25 heart beats. Further, in one or more embodiments, the physiological response may be monitored over a selected number of heart beats such as, e.g., greater than or equal to about 2 heart beats, about 3 heart beats, about 5 heart beats, about 8 heart beats, about 10 heart beats, etc.

In one or more embodiments, determining that a fault exists 210 may include analyzing the monitored physiological response over a selected number of heart beats. If a physiological response is detected, or is outside a range of expected behavior, for a portion (e.g., selected number or ratio) of the selected number of heart beats, then it may be determined that a fault exists associated with the pacing therapy. In other words, instead of analyzing a physiological response for a single heart beat, the physiological response over a period of time, or number of heart beats, may be analyzed. Further, a specific threshold used to switch to a pace recovery mode can be adjusted (e.g., n missed beats, x of y missed beats, etc.) and/or may be optimized for each individual patient.

Further, the exemplary method 200 may periodically initiate 212 sensing of at least one physiological response during delivery of pacing therapy 202 without being triggered by identification of at least one suspect parameter 206. For example, once every 100 heart beats, the method 200 may trigger sensing of a physiological response to pacing 208.

Since the sensing of a physiological response during delivery of pacing therapy 208 may be periodically initiated 212, the potentially fault-triggered initiation of sensing of a physiological response during the delivery of pacing 208, e.g., from the identification of at least one suspect parameter 206, may be described has interrupting, or bypassing, the periodic initiation 212 of sensing. In other words, the fault-triggered initiation of sensing of a physiological response during the delivery of pacing may increase the amount of physiological response sensing that normally occurs (e.g., greater than would normally occur). Further, for example, the fault-triggered initiation of sensing of a physiological response during the delivery of pacing 208 may occur at different times than under the periodic initiation 212 of sensing (e.g., fault-triggered initiation of sensing of a physiological response during the delivery of pacing 208 may occur at any time while the periodic initiation 212 of sensing may only occur periodically).

Figure 8:
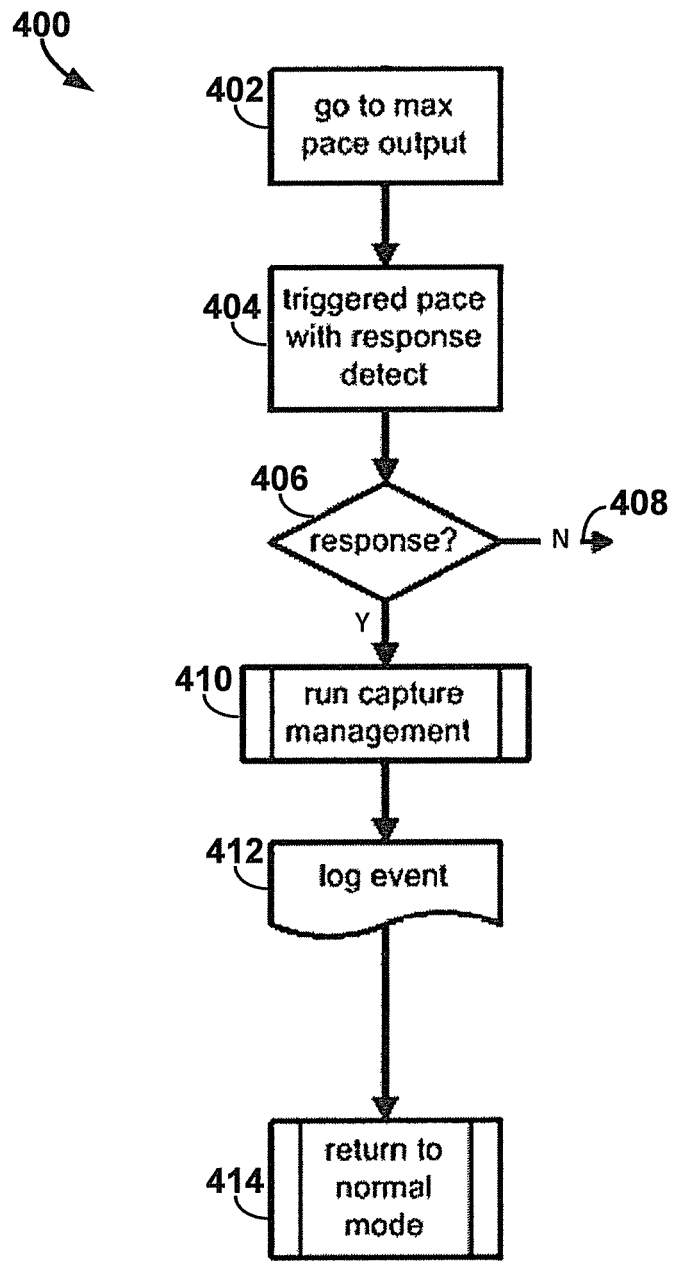
FIG. 8 is a flow chart of an exemplary method of pacing recovery from FIG. 5.
Figure 9:
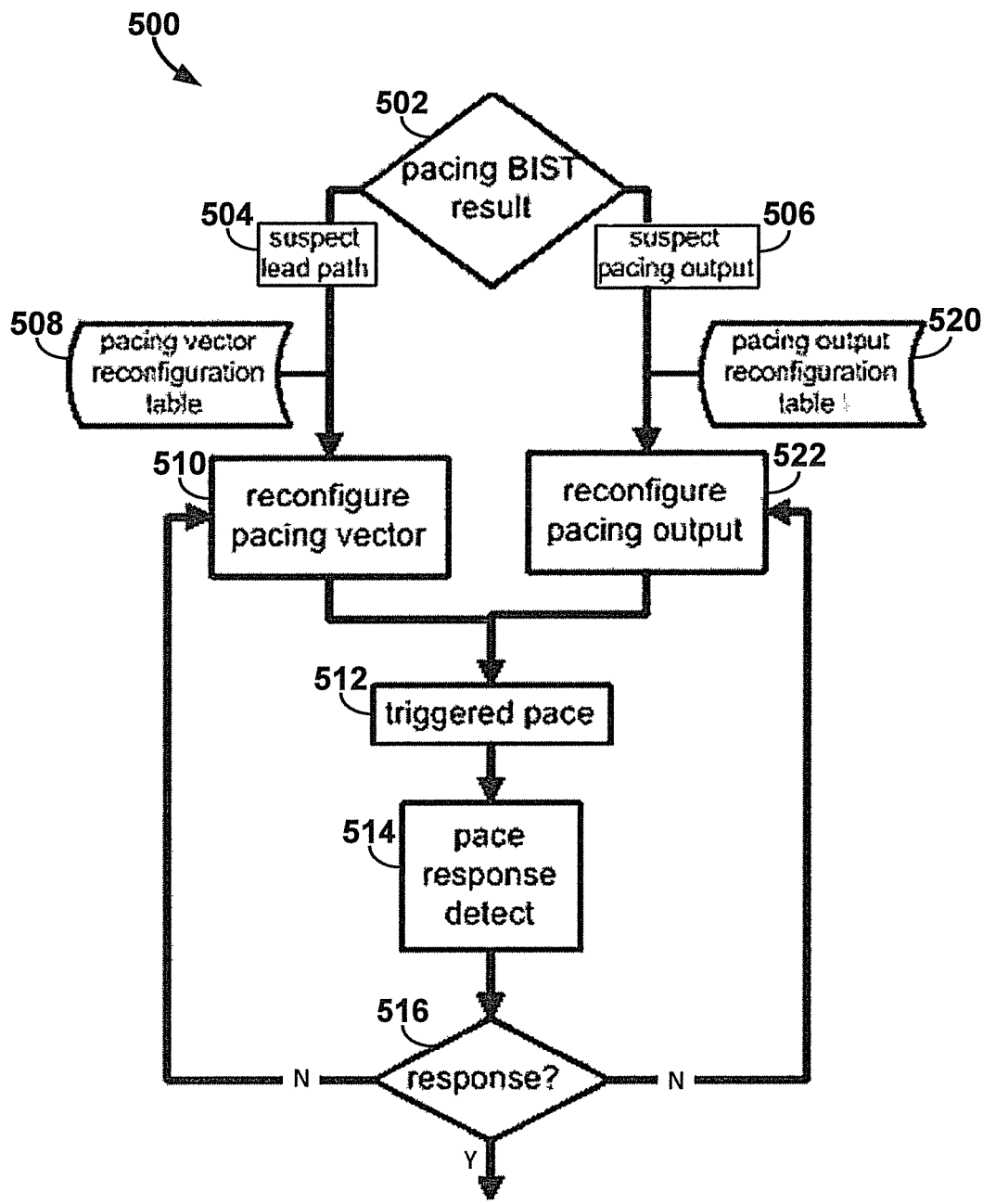
FIG. 9 is a flow chart of an exemplary method of fault handling from FIG. 5.
Figure 10:
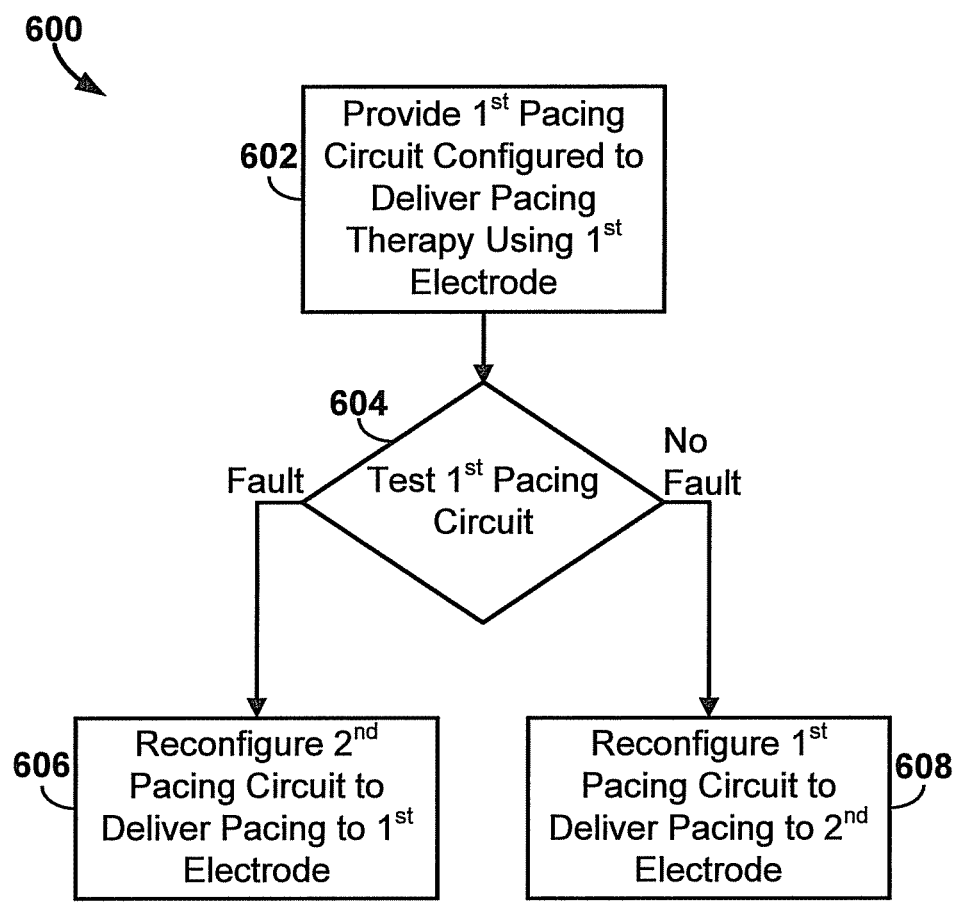
FIG. 10 is a flow chart of another exemplary method of fault handling from FIG. 5.

If a fault is determined to exist 210, the exemplary method 200 may proceed to pacing recovery as described herein with reference to FIG. 8 and potentially fault recovery as described herein with reference to FIGS. 9-10. If a fault 210 is not determined to exists, the exemplary method 200 may continue, or return to, providing pacing therapy 202 and monitoring one or more parameters 204 associated with the device providing pacing therapy.

Figure 7:
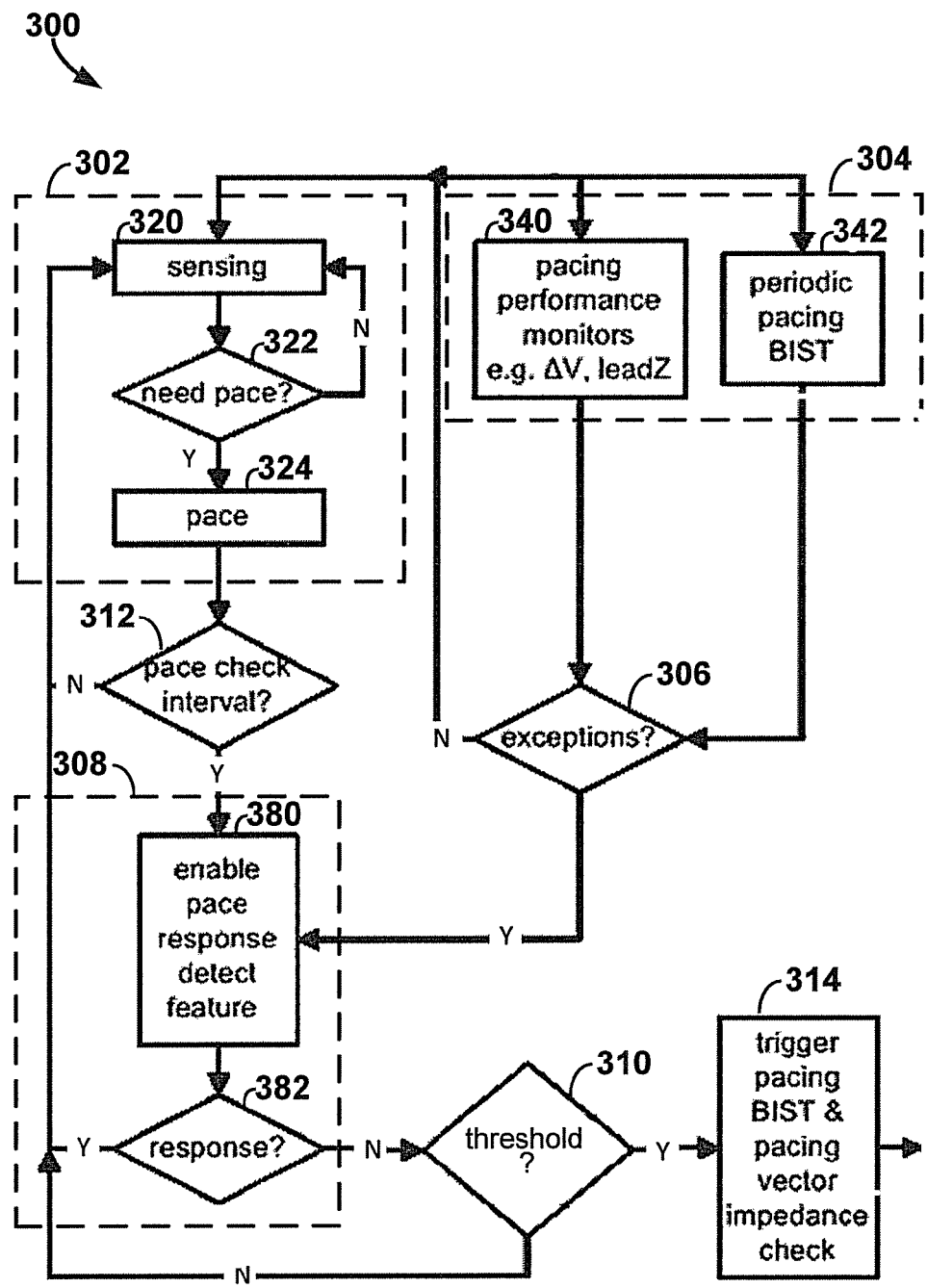
FIG. 7 is a flow chart of another exemplary method of fault determination from FIG. 5.

Another exemplary method 300 of fault detection is depicted in FIG. 7. Similar to exemplary method 200 of FIG. 6, exemplary method 300 includes delivering pacing therapy 302, monitoring one or more parameters of a pacing device 304, e.g., IMD 16, identifying a suspect parameter, or exception, indicative of a fault 306, sensing a physiological response of the patient during the delivery of pacing therapy 308, and periodically initiating 312 the sensing of a physiological response of the patient during the delivery of pacing therapy.

As shown in more detail, providing pacing therapy 302 may include sensing one or more cardiac parameters 320, determining whether or when a pace is needed 322, and delivering a pace 324 if a pace is needed. The exemplary method 300 may periodically trigger 312, at a pace check interval, monitoring a physiological response during pacing therapy 308.

Further as shown in more detail, monitoring one or more parameters of a pacing device 304 may include monitoring one or more pacing performance parameters 340 and conducting a BIST 342 (e.g., periodically). The one or more monitored pacing performance parameters, BIST results, and any other monitored parameters of the pacing device, or system, may be analyzed to determine suspect, or exceptional, parameters 306 (also referred to as suspects or exceptions). When a suspect, or exception, is identified, the method 300 may trigger, or initiate, the sensing of a physiological response to pacing 308.

Sensing a physiological response during pacing therapy 308 may include enabling a pace response detection feature 380 and monitoring whether a physiological response occurs during the pacing 382. As depicted, the exemplary method 300 may further include determining whether a fault exists based on the at least one physiological response using a threshold 310. In at least one embodiment, the threshold may include a ratio representative of an amount of responses needed over a selected period of time to determine if one or more faults exists. For example, if a response is not detected in 3 out of 4 heart beats, then it may be determined that one or more faults exist.

Further, if it is determined that one or more faults exist 310, the exemplary method 300 may further include performing diagnostics of internal pacing circuitry and one or more leads 314, e.g., such as triggering a built-in self-test (BIST) and pacing vector impedance check, for use in determining where the one or more faults may be located. For example, the BIST may determine that the fault exists in one of the pacing output circuits, or the pacing vector impedance check may determine that the fault exists in one of the lead circuits. Such determinations may be useful in fault recovery and/or fault handling.

If the detection algorithm determines that the pacing pulses are not triggering the appropriate physiological response, a pace recovery mode may be invoked. The purpose of a pace recovery mode is to ensure that pacing therapy is restored as quickly as possible. In some instances, the only needed change may involve a change in pacing amplitude. In at least one embodiment, the first phase may be to temporarily increase the pacing output voltage to the maximum value available from the system and/or increase the pacing pulse duration. This temporary change in the pacing amplitude should have no adverse impact on the patient. The system will continue to monitor for a physiological response. If a physiological response is restored under these temporary pacing settings, the system can begin to re-optimize by running a capture management type algorithm to reduce the pacing amplitude in order to maximize device longevity. If the system continues to observe the desired response to pacing stimuli, the system may then be restored to a normal mode.

An exemplary method of pacing recovery 400 is depicted in FIG. 8. Exemplary method 400 may be triggered when a fault is determined to exist, e.g., using the fault detection, or determination, methods and/or processes described herein with reference to FIGS. 6-7. Pacing recovery mode 400 may include modifying the pacing therapy by changing at least one parameter of the pacing therapy such as setting a pacing output to a maximum 402. Setting the pacing output to a maximum 402 may include changing one or more parameters of the pacing therapy such as pacing amplitude, frequency, voltage, burst/pulse length, pacing energy (e.g., using an additional pacing capacitor), etc. In at least one embodiment, setting the pacing output to a maximum 402 includes increasing the pacing amplitude of the pacing therapy to a maximum value (e.g., 8 volts for a 2 millisecond pulse).

After the pacing output has been set to a maximum 402, the method 400 may trigger pacing therapy 404 using the changed, e.g., maximum, settings and also monitor, or sense, at least one physiological response 406 of the patient during the pacing therapy. If no response is detected, or a detected response is determined to be unacceptable (e.g., the detected response indicates that the pacing therapy is insufficient to regulate a patient's heart), the exemplary method 400 may proceed to one or more fault handling methods and/or processes 408.

If a response is detected (e.g., an acceptable response indicating that the pacing therapy is sufficient to regulate a patient's heart), the method 400 may proceed to run one or more capture management processes and/or methods 410 to sufficiently capture the patient's heart to provide regulation of the patient's heart (e.g., determine adequate pacing parameters, reduce pacing amplitude to determine if adequate and keep reduced pacing amplitude if adequate, reduce other various pacing parameters until desired level of parameters is achieved and capture still exists, etc.). After the capture management processes and/or methods have been run 410, the method 400 may log the event 412 and return to normal pacing mode 414 (e.g., block 202 of FIG. 6, at new pacing parameters). For example, data (e.g., dates, times, one or more parameters of the pacing therapy, one or more physiologically monitored parameters of the patient, etc.) related to the determined one or more faults and/or the pacing recovery processes may be logged, e.g., such that the events may be viewed by a clinician at a later time.

If changes in one or more pacing parameters, or settings, during pacing recovery processes and/or methods (e.g., exemplary methods 400 described herein with reference to FIG. 8) do not elicit a desired physiological response, or if a BIST of the pacing output circuitry returns indications of a potential fault condition, the exemplary methods and/or systems described herein may determine that a fault has occurred, e.g., potentially in the generator, the lead pathway, the lead/patient interface, or in the patient (such as, e.g., an exit block). The exemplary methods and/or system may then be tasked with reconfiguring the pacing pathway in order to return to at least a minimal state of pacing support, namely right ventricular (RV) pacing, even if it means halting right atrial (RA) or left ventricular (LV) pacing vectors in order to deliver basic RV pacing support. A variety of options can be made available, namely in the areas of pacing output circuitry functionality (e.g., if the system is actually generating pacing pulses and getting them out to the lead) or lead pathway integrity (e.g., if the lead or connection is broken somewhere thus preventing the pacing pulse from getting to the patient). In other words, if a fault is detected associated with the IMD delivering pacing therapy, the exemplary methods and/or systems described herein may proceed to handle the one or more faults.

An exemplary method of fault handling 500 is depicted FIG. 9. Using data collected during a BIST 502, or any other one or more monitored parameters indicative of one or more faults associated with an IMD, the exemplary method 500 may determine whether a fault exists in one or more leads (e.g., suspect lead path) 504 or one or more pacing output circuits (e.g., suspect pacing output) 506.

For example, if an electrode, e.g., tip electrode of a LV lead, is indicated as not delivering pacing therapy that elicits a sufficient physiological response, the lead providing pacing therapy to the electrode and the pacing output circuit providing pacing therapy to the lead may be evaluated, or tested. In one or more embodiments, the method 500 may utilize test results, or one or more monitored parameters, from a fault-detection method such as the exemplary methods described herein with reference to FIGS. 6-7.

In at least one embodiment, a BIST may be used. If the BIST indicates a short in a pacing output circuit, then the fault is in the pacing output circuit (e.g., a suspect pacing output 506). If the BIST does not indicate any problems with any pacing output circuits, then the fault may be in the lead (e.g., a suspect lead path 504).

If the fault is indicated to be in the lead 504, or the lead path is suspect, (e.g., the lead may have become broken, dislodged, etc.), then the electrode configuration may be modified using, e.g., a pacing vector reconfiguration table 508. More specifically, the pacing therapy normally delivered by a pair of electrodes (e.g., a pacing vector) may be reconfigured 510 to use at least one different electrode, e.g., to replace a non-functional electrode, to deliver the pacing therapy (e.g., pacing therapy directed to the same target tissue such as the LV but using a different pacing vector).

Further, as described herein, different portions of a patient's heart may have different priorities. In other words, different portions of a patient's heart may be more crucial to receive pacing therapy. For example, right ventricular (RV) pacing often has a high priority. If an electrode providing RV pacing is determined to be non-functional, e.g., due to a fault in the lead, lead dislodgement, etc., RV pacing may be reconfigured to use one or more electrodes different than at least one electrode previously delivering RV pacing that has been determined to be at fault. The electrical path between the two electrodes used to deliver pacing may be referred to as the pacing vector. As such, reconfiguring the RV pacing to use different electrodes may be referred to as changing the RV pacing vector.

In at least one embodiment, pacing may be delivered via a bipolar configuration between an RV lead tip electrode and an RV lead ring electrode, or in some cases between a RV lead tip electrode and housing electrode (e.g., electrode 58 of IMD 16). Depending upon the device and lead configuration in the patient (e.g., single chamber, dual chamber, triple chamber, pacemaker vs. defibrillation platform, etc.), one or more options may be available.

An exemplar pacing reconfiguration table is shown below in Table 1, which provides a list of primary and potential alternative pacing vectors. The construction of the pacing reconfiguration table can be created a priori, or built in-situ, during normal operation where a periodic evaluation of different pathway parameters, such as alternative pathway impedance trends or periodic alternative site pacing capture management analysis is invoked, in order to preemptively queue up the alternative pacing vector configuration table in preparation for potential pacing pathway reconfigurations.

TABLE 1

Exemplary Pacing Reconfiguration Table for Right Ventricular Pacing

|  | single chamber | dual chamber | triple chamber |
|---|---|---|---|
| primary | RVtip→RVring | RVtip→RVring | RVtip→RVring |
| alternative 1 | RVtip→CAN (IPG) | RVtip→CAN (IPG)/ | RVtip→CAN (IPG) |
|  | RVtip→RVC (ICD/CRT-D) | RVtip→RVC (ICD/CRT-D) | RVtip→RVC (ICD/CRT-D) |
| alternative 2 | RVring→RVC | RVring→RVC | LVtip→LVringx (LV only pacing), e.g. |
| alternative 3 etc. | RVring→CAN | RVring→CAN RVring→RAtip, etc. | LVtip→RVring RVring→RAtip, etc. |

Depending on the number of chambers and device configurations (e.g., implantable pulse generator (IPG) versus implantable cardiac defibrillator (ICD), cardiac resynchronization therapy pacemaker (CRT-P) versus cardiac resynchronization therapy defibrillator (CRT-D)), various alternates will be viable and/or available for use.

For example, in a single chamber configuration, if the RV pacing vector using the RV lead tip electrode (RVtip) and the RV lead ring electrode (RVring) is determined to be at fault, the first alternative may reconfigure the pacing vector to replace the RV lead ring electrode with the housing, or can, electrode (CAN) in an IPG system, or the RV coil electrode (RVC) in an ICD/CRT-D system. The second alternative, e.g., if the first alternative is unsuccessful (e.g., incapable of providing, or eliciting, a physiological response), may reconfigure the pacing vector to replace the RV lead tip electrode with the RV lead ring electrode and the RV lead ring electrode with the RV lead coil electrode (e.g., in both an IPG and ICD/CRT-D systems if they have an RV coil electrode). The third alternative, e.g., if the first and second alternatives are unsuccessful (e.g., incapable of providing, or eliciting, a physiological response), may reconfigure the pacing vector to replace the RV lead tip electrode with the RV lead ring electrode and the RV lead ring electrode with the housing, or can, electrode (e.g., in both an IPG and ICD/CRT-D systems).

In other words, an exemplary pacing reconfiguration table may be a series of potential pacing vectors available to the pacing devices and/or system. Each device and/or system may include a primary, or preferred, pacing vector that would normally be used, but the device and/or system may be configured to be able to select alternative vectors until a suitable configuration is found with good capture.

In at least one embodiment, the exemplary methods and devices may pre-emptively and periodically test the efficiency and/or efficacy of the various different pacing vectors found within the pacing reconfiguration table and record relevant information (e.g., capture information) with respect to each vector such as pacing voltage needed to pace using that particular vector (e.g., a minimum voltage, etc.). In other words, the pacing reconfiguration table may be periodically updated. As such, the methods and devices may have a predetermined idea of which alternative vectors and what settings should be tried first in the event that a pacing vector with a potential fault is detected and requires reconfiguration. In essence, the pacing reconfiguration table may include more information than prioritized, or ranked, vector information such as pacing parameters for each vector that are known to effectively deliver pacing therapy. Further, based on the preemptive and periodic tests, the rankings of the vectors may be reorganized based on efficiency and/or effectiveness (e.g., if the performance of the different vectors changes over time).

The selection and reconfiguration of the pacing vectors may be governed by firmware with appropriate modifications in hardware. Exemplary devices and/or systems would store information about the reconfiguration and provide that information as part of an alert and/or routine system download, depending on the criticality of the reconfiguration.

After the pacing vector has been reconfigured 510, the exemplary method 500 may trigger a pacing pulse 512 using the reconfigured pacing vector and monitor a physiological response of the patient (pace response detect) 514. If a response is elicited 516, the method 500 may return to run one or more capture management processes and return to normal pacing operation using the reconfigured pacing vector. Further, the one or more pacing parameters of the normal pacing operation may have been adjusted by the one or more capture management processes. If capture management is not available or not utilized prior to returning to normal pacing operation, the pacing therapy may be configured for maximum energy output. If a response is not elicited 516, the method 500 may return to reconfiguring the pacing vector 510 until a pacing vector is found to elicit a physiological response. In other words, the exemplary method 500 may continue to reconfigure pacing vectors until a reconfigured pacing vector is successful in delivering pacing therapy (e.g., such that a suitable physiological response occurs in response to the pacing therapy).

Further, in at least one embodiment, if all the pacing vectors are exhausted (e.g., all the alternative pacing vectors in a pacing vector reconfiguration table) without success, the exemplary method 500 may return to the original pacing vector and try pacing output reconfiguration 522 (e.g., even though it was originally determined that the fault existed in the lead path). If pacing output reconfiguration also fails, the exemplary method 500 may return to the originally programmed settings/configurations and issue an alert (e.g., at least some level of notification may be issued). In at least one embodiment, where multiple pacing vectors are attempted without success or when the system reconfigures pacing circuitry to provide RV pacing and loses the ability to pace in the RA, or if biventricular pacing is lost, a notification/alarm may be issued.

In other instances, the loss of pacing may not be due to the pathway, but may be due to a loss of pacing output circuitry function or some pathway on the hybrid (e.g., the IMD) itself. Upon recognition that a pacing pulse is not resulting in physiological response, the output circuitry and on-hybrid pathway can be checked, possibly using a form of a BIST, to determine if pacing output function and/or the hybrid pathway are at fault. If the pacing output, or the on-hybrid routing, is determined to be suspect, then the fault-tolerant configuration can automatically switch out the suspect circuit/path to one of other available outputs.

For example, in method 500, if it is determined 502 that one or more faults exists in one or more pacing output circuits 506, then one or more pacing output circuits may be reconfigured 522 using, e.g., a pacing output reconfiguration table 520. More specifically, a pacing vector (e.g., a pair of electrodes) normally receiving pacing output, or pacing pulses, delivered by a pacing output circuit that is determined to be at fault may be reconfigured to use a different pacing output circuit, e.g., to replace the non-functional pacing output circuit.

Similar to the pacing reconfiguration table 508, the pacing output reconfiguration table 520 may also be prioritized based on what pacing vectors are most important (e.g., RV pacing may have the highest priority). As such, if a pacing output circuit is delivering pacing therapy to an important pacing vector (e.g., pacing vectors having a higher priority than others) and that pacing output circuit is determined to be at fault, another pacing output circuit (e.g., which may be less important) may be configured to deliver pacing therapy to the important pacing vector.

Also similar to the pacing vector reconfiguration, after the pacing output circuit has been reconfigured 522, the exemplary method 500 may deliver a pacing pulse 512 using the reconfigured pacing output circuit and monitor a physiological response of the patient (pace response detect) 514. If a suitable, or acceptable, response is elicited 516, the method 500 may return to run one or more capture management processes and return to normal pacing operation using the reconfigured pacing output circuit. If a suitable response is not elicited 516, the method 500 may return to reconfiguring the pacing output 522 until a pacing output circuit is found that elicits a suitable physiological response. In other words, the exemplary method 500 may continue to reconfigure pacing output circuits until the pacing is successful (e.g., such that a suitable, or acceptable, physiological response occurs in response to the pacing therapy).

In at least one embodiment, if all the pacing output configurations are exhausted (e.g., all the alternative pacing output reconfigurations in a pacing output reconfiguration table have been tried) without success, the exemplary method 500 may return to the original pacing output configuration and try pacing vector reconfiguration 508 (e.g., even though it was determined that the fault existed in the pacing output circuit). In at least one embodiment, an alarm may be issued if all the pacing output configurations are exhausted without success.

An exemplary fault handling method 600 for reconfiguring pacing output circuits is depicted in FIG. 10. Exemplary method 600 includes providing a first pacing output circuit configured to deliver pacing therapy using a first electrode 602 (e.g., an electrode in a pair of electrodes for delivering pacing to a pacing vector) and testing the first pacing output circuit 604 (e.g., using a BIST). If the first pacing output circuit is determined to be at fault (e.g., a fault is determined to exist in the first pacing output circuit), then a second pacing output circuit may be reconfigured to delivering pacing therapy using the first electrode 606. Further, although not depicted, the first pacing output circuit may also be reconfigured such that it is no longer used or activated.

If the first pacing output circuit is not determined to be at fault (e.g., a fault is not determined to exist in the first pacing output circuit), then it may be determined that the first electrode is at fault (e.g., dislodged, etc.), and therefore, the first pacing output circuit may be reconfigured to delivering pacing therapy using a second electrode 608. Further, although not depicted, the first electrode may also be reconfigured such that it is no longer used or activated.

Figure 11B:
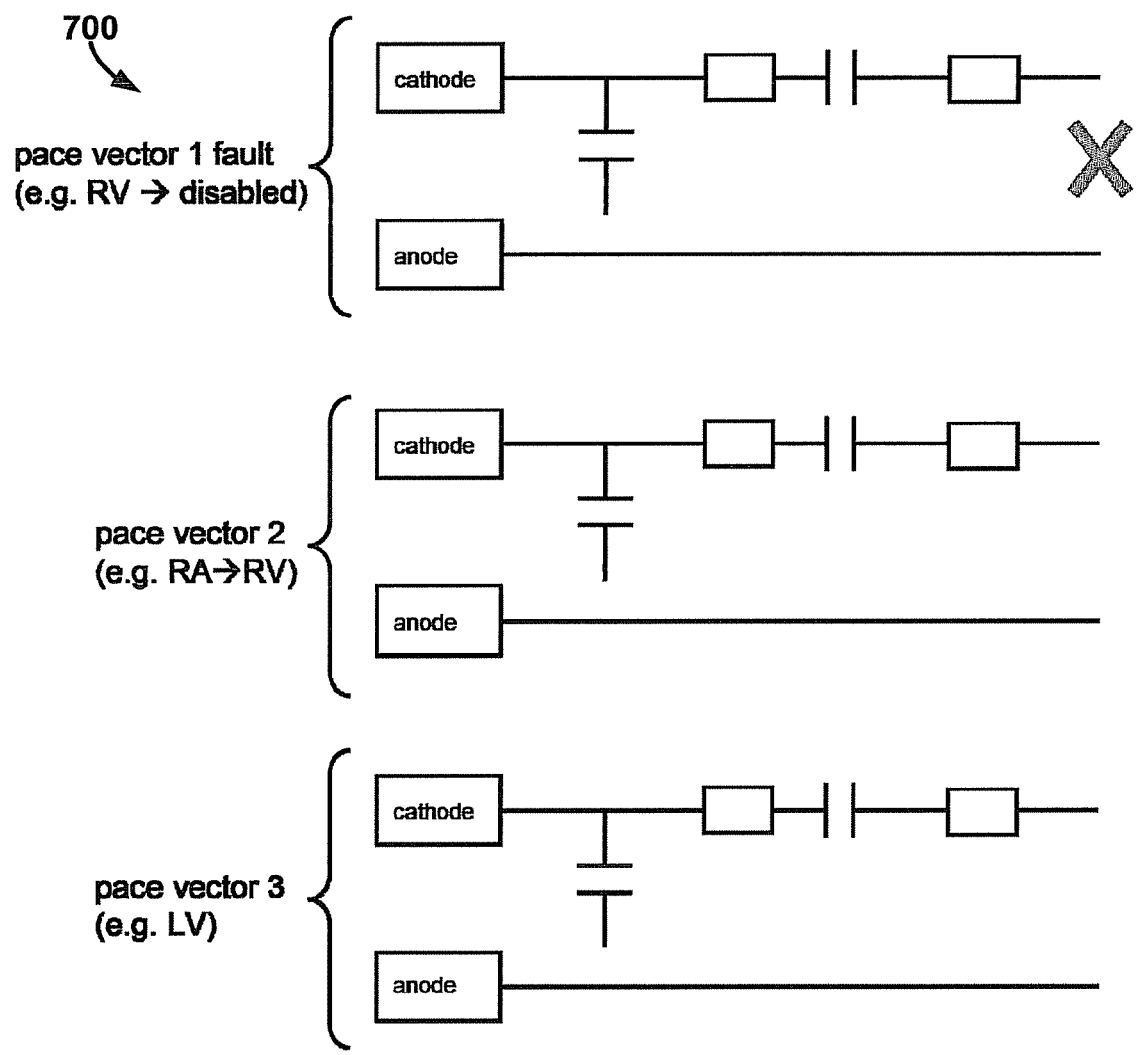
Figure 11C:
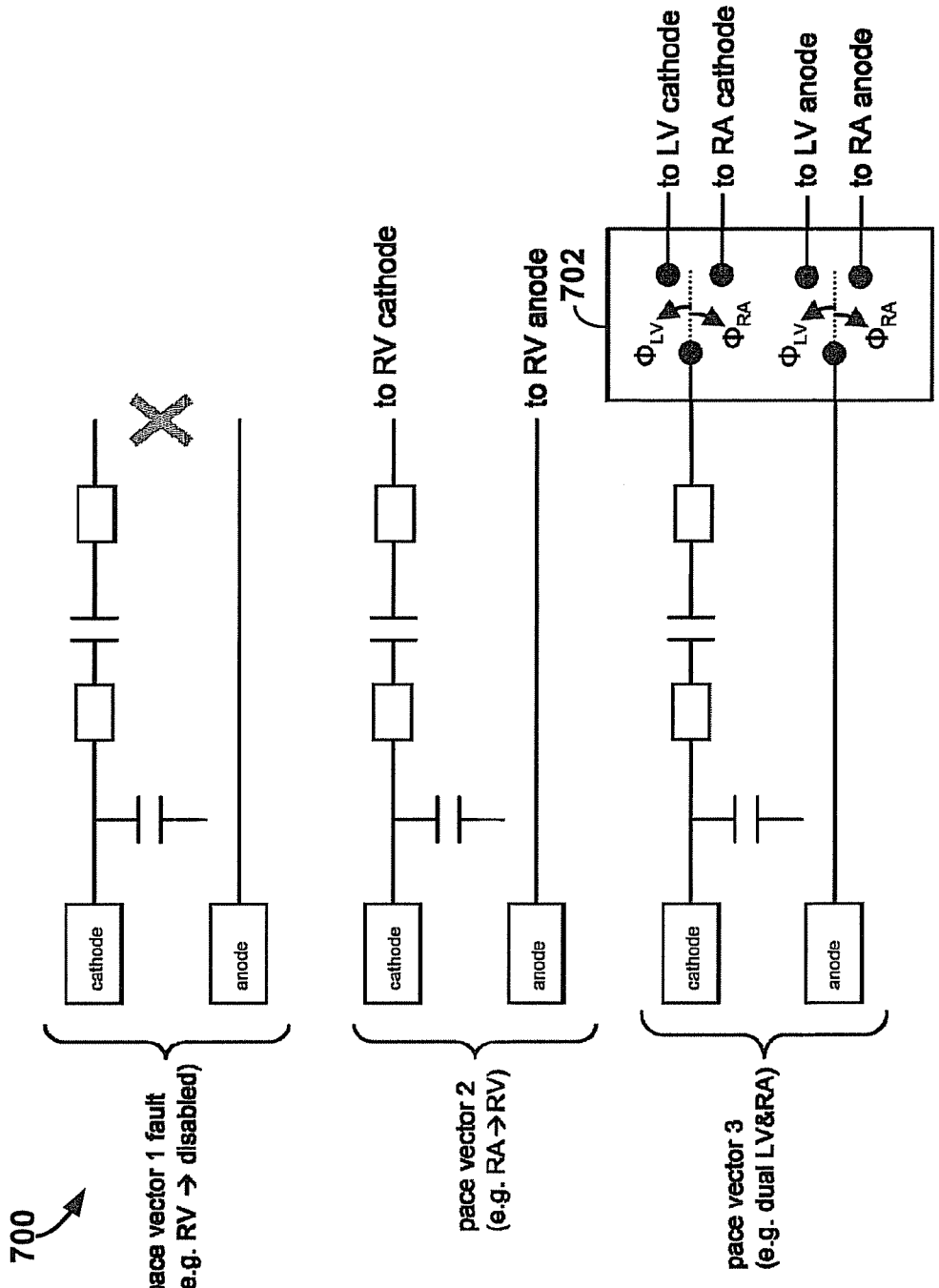

A diagram illustrating an exemplary pacing output circuit reconfiguration is depicted in FIGS. 11A-11B. The pacing output configuration 700 before reconfiguration is depicted in FIG. 11A, and the pacing output configuration 700 after reconfiguration is depicted FIG. 11B. As shown in FIG. 11A, a pacing output circuit may be configured to deliver pacing therapy using pace vector 1 to the RV, a pacing output circuit may be configured to deliver pacing therapy using pacing vector 2 to the RA, and a pacing output circuit may be configured to deliver pacing therapy using pacing vector 3 to the LV.

If it is determined that the pacing output circuit delivering pacing therapy using pacing vector 1 to the RV is at fault, it may be disabled as shown in FIG. 11B. Further, since in this example, the RV pacing has priority over RA pacing, the pacing output circuit delivering pacing therapy using pacing vector 2 to the RA may be reconfigured to deliver pacing therapy to the RV (e.g., the pacing pulses, timings, etc. may be modified for RV pacing therapy). Also, as shown, the pacing output circuit delivering pacing therapy using pacing vector 3 to the LV may be unchanged (e.g., not reconfigured).

In other words, if the loss of RV pacing is detected and it is determined that it is caused by the pacing output circuit delivering pacing to the RV pacing vector, then the pacing circuit for the right atrium (RA), if present, can be modified and rerouted to provide the RV pacing (with the potential loss of RA pacing support). Due to the need in some patients for basic RV pacing, viability of the RV pacing vector may take priority over other pacing modalities.

As shown, additional hardware may not be needed to achieve the fail-safe mission of providing basic pacing therapy. This stand-by fail-safe configuration could be implemented without relying on additional discrete components in the system. Further, the level of configurability is performed at the circuit level. Additional levels of fault-tolerance could be included to provide redundancy at the component level, but this illustrated example minimizes the need for any additional hardware and can be accomplished with a firmware algorithm and a configurable switching change to reassign and redirect the pacing output vectors to more critical channels.

Additional fault-tolerance can be provided by dual use of a single pacing output circuit to cover multiple pacing vectors. The pacing output configuration 700 after dual use reconfiguration is depicted FIG. 11C. As shown, if it is determined that the pacing output circuit delivering pacing therapy using pacing vector 1 to the RV is at fault, it may be disabled. Further, similar to the configuration shown in FIG. 11B, since the RV pacing has priority over RA pacing, the pacing output circuit delivering pacing therapy using pacing vector 2 to the RA may be reconfigured to deliver pacing therapy to the RV (e.g., the pacing pulses, timings, etc. may be modified for RV pacing therapy).

In this embodiment, the pacing output circuit delivering pacing therapy using pacing vector 3 to the LV may also be reconfigured to deliver pacing therapy to both the RA and the LV using a switch 702 (e.g., similar to the switch module 85 of IMD 16). Since RA and LV pacing signals are not usually simultaneous, the switch 702 may route, or configure, the pacing output circuit delivering RA pacing to the pacing vector 3 during a time period for RA pacing and may route, or configure, the pacing output circuit delivering LV pacing to the pacing vector 3 during a time period for LV pacing.

In other words, if the pace vector 1 (RV) pacing circuit is lost due to some fault, the remaining viable pacing output circuits can be reconfigured to potentially provide full pacing coverage. This can be accomplished by disabling the faulty pace vector 1 output, reconfiguring the pace vector 2 (RA) pacing circuit to cover the RV channel (now dedicated to the RV since it is may be safety critical), and assigning the pace vector 3 (LV) circuit to provide both pacing signals to the RA as well as LV. The redirection of the pacing output energy may be handled by an output mux to steer the delivered energy to the appropriate lead pathway during the appropriate time intervals (denoted as $\phi_{LV}$ and $\phi_{RA}$).

Dual use of a single pacing output circuit to cover multiple pacing vectors may be described in reference to exemplary method 600 of FIG. 10. For example, if the second pacing output circuit is reconfigured to deliver pacing therapy to the first electrode, the second pacing output circuit may be configured to deliver pacing therapy to the first electrode during a first time period and to deliver pacing therapy to the second electrode during a second time period where the first time period and the second time period do not overlap.

Further, in at least one embodiment, a third pacing output circuit and third electrode may be utilized. For example, if one pacing output circuit out of three pacing output circuits is determined to have a fault, the two remaining functioning pacing output circuits may be configured to deliver pacing therapy to the three electrodes. One of the two remaining functioning pacing output circuits may be configured to deliver therapy to the pacing vector with the highest priority while the other remaining functioning pacing output circuit may be configured to deliver therapy to both the remaining pacing vectors having lower priority.

In at least one embodiment, to reduce the complexity and challenges posed by different pacing thresholds that may be exhibited by the different pacing vectors, the fault-tolerant configurations can simply supply the same pacing output voltage to both of the covered channels, defaulting to the higher pacing threshold (or even higher) in order to ensure capture in both locations (e.g., if RA threshold is 0.5V and LV is 1.5V, then the fault-configured dual-use output circuit could simply provide 1.5V to both outputs during their appropriate pacing pulses).

For example, in one embodiment, if first pacing output circuit is determined to be at fault, and a second pacing output circuit is to be reconfigured to deliver pacing therapy to a pacing vector originally associated with the first pacing circuit, then the voltage of the pacing therapy delivered by the second pacing output circuit may be set, or configured, to be the higher of the voltage of the pacing therapy delivered using the first, non-functional pacing output circuit and the voltage of the pacing therapy delivered using the second pacing output circuit. This configuration may provide capture in both chambers.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A fault detection method for use in detecting one or more faults associated with an implantable medical device that require action to be taken for handling of the one or more faults, the method comprising:

delivering pacing therapy to a patient using an implantable medical device;

monitoring one or more parameters of the implantable medical device during the delivery of pacing therapy;

identifying at least one suspect parameter in the one or more monitored parameters indicative of one or more faults associated with the implantable medical device that require action to be taken for handling of the one or more faults, wherein, to identify at least one suspect parameter in the one or more monitored parameters indicative of one or more faults, the control module is further configured to execute one or more of analyzing clock speed, testing internal pacing circuitry, and testing discrete component leakage;

sensing at least one physiological response of the patient during the delivery of pacing therapy in response to identifying the at least one suspect parameter prior to initiating action to handle the one or more indicated faults; and determining whether a fault exists based on the at least one physiological response sensed during delivery of pacing therapy in response to identifying the at least one suspect parameter prior to initiating action to handle the one or more indicated faults.

2. The method of claim 1, further comprising:
delivering pacing therapy to a patient using the implantable medical device, wherein the implantable medical device comprises:
a housing,
a first electrode and a second electrode,
a first pacing output circuit located within the housing, wherein the first pacing output circuit is configured to deliver pacing therapy to the patient using the first electrode, and
a second pacing output circuit located within the housing, wherein the second pacing output circuit is configured to deliver pacing therapy to the patient using the second electrode;
determining if a fault exists in the first pacing output circuit; and
reconfiguring the second pacing output circuit to deliver pacing therapy using the first electrode if a fault is determined to exist in the first pacing output circuit.

3. The method of claim 2, wherein the method further comprises:
delivering pacing therapy with the first electrode using the second pacing output circuit during a first time period; and
delivering pacing therapy with the second electrode using the second pacing output circuit during a second time period, wherein the first time period and the second time period do not overlap.

4. The method of claim 3, wherein the method further comprises setting the voltage of the pacing therapy delivered by the second pacing output circuit to the higher of the voltage of the pacing therapy delivered with the first electrode using the first pacing output circuit and the voltage of the pacing therapy delivered with the second electrode using the second pacing output circuit.

5. The method of claim 2, wherein the implantable medical device comprises a third electrode and a third pacing output circuit located in the housing, wherein the third pacing output circuit is configured to deliver pacing therapy to the patient using the third electrode,
wherein the method comprises reconfiguring the third pacing output circuit to deliver pacing therapy with at least one of the second electrode and the third electrode if a fault is determined to exist in the first pacing output circuit.

6. The method of claim 5, wherein the method further comprises:
delivering pacing therapy with the second electrode using the third pacing circuit during a first time period; and
delivering pacing therapy with the third electrode using the third pacing circuit during a second time period, wherein the first time period and the second time period do not overlap.

7. The method of claim 2, wherein determining if a fault exists in the first pacing output circuit comprises testing the first pacing output circuit.

8. The method of claim 2, wherein the method further comprises reconfiguring the first pacing output circuit to deliver pacing therapy with the second electrode if no fault is determined to exist in the first pacing output circuit.

9. The method of claim 2, wherein the first electrode is configured to deliver pacing therapy to the patient's right ventricle.

10. The method of claim 1, wherein the method further comprises:
modifying the pacing therapy by changing at least one parameter of the pacing therapy in response to determining that a fault exists;
sensing at least one physiological response of the patient during delivery of the modified pacing therapy; and
performing fault handling operations if the at least one sensed physiological response of the patient during delivery of the modified pacing therapy is not an expected physiological response in response to the delivery of the modified pacing therapy.

11. The method of claim 10, wherein changing at least one parameter of the pacing therapy comprises changing the pacing therapy to a maximum output for the pacing therapy using the implantable medical device.

12. The method of claim 1, wherein sensing at least one physiological response of the patient during the delivery of pacing therapy comprises sensing the at least one physiological response of the patient during the delivery of pacing therapy over a selected number of heart beats, and
wherein determining whether a fault exists comprises determining whether a fault exists based on the at least one physiological response sensed during the delivery of pacing therapy over the selected number of heart beats.

13. The method of claim 1, wherein determining whether a fault exists based on the at least one physiological response sensed during the delivery of pacing therapy comprises determining whether the at least one sensed physiological response is an expected physiological response in response to the delivery of pacing therapy.

14. The method of claim 1, wherein the method further comprises performing diagnostics of internal pacing circuitry and one or more leads of the implantable medical device to determine if the detected fault is associated with one of the internal pacing circuitry and the one or more leads in response to determining that a fault exists.

15. The method of claim 1, wherein identifying at least one suspect parameter in the one or more monitored parameters indicative of one or more faults comprises analyzing at least one of delivered pacing capacitor energy and lead impedance.

16. The method of claim 1, wherein identifying at least one suspect parameter in the one or more monitored parameters indicative of one or more faults further comprises testing of a power supply.

17. The method of claim 1, wherein, to handle a determined fault, the method further comprises reconfiguring at least one of an electrode vector configuration according to a periodically-updated pacing reconfiguration table and pacing output circuit configuration for the pacing therapy in response to determining that a fault exists.

18. A fault detection method for use in detecting one or more faults associated with an implantable medical device that require action to be taken for handling of the one or more faults, the method comprising:
delivering pacing therapy to a patient using an implantable medical device;
monitoring one or more parameters of the implantable medical device during the delivery of pacing therapy;

identifying at least one suspect parameter in the one or more monitored parameters indicative of one or more faults associated with the implantable medical device that require action to be taken for handling of the one or more faults;

sensing at least one physiological response of the patient during the delivery of pacing therapy in response to identifying the at least one suspect parameter prior to initiating action to handle the one or more indicated faults; and determining whether a fault exists based on the at least one physiological response sensed during delivery of pacing therapy in response to identifying the at least one suspect parameter prior to initiating action to handle the one or more indicated faults, wherein the method further comprises periodically sensing at a periodic sensing rate at least one physiological response of the patient during the delivery of pacing therapy for use in determining whether a fault exists, wherein sensing at least one physiological response of the patient during delivery of pacing therapy in response to identifying the at least one suspect parameter interrupts the periodic sensing at the periodic sensing rate.

19. An implantable medical device for use in delivering pacing therapy to a patient comprising:
a therapy delivery module configured to deliver pacing therapy to a patient;
sensing apparatus configured to monitor at least one physiological response of the patient in response to the delivery of pacing therapy; and
a control module coupled to the therapy delivery module and to the sensing apparatus and configured to:
initiate the delivery of pacing therapy to the patient,
monitor one or more parameters of the implantable medical device during the delivery of pacing therapy,
identify at least one suspect parameter in the one or more monitored parameters indicative of one or more faults associated with the implantable medical device that require action to be taken for handling of the one or more faults,
sense, using the sensing apparatus, at least one physiological response of the patient during the delivery of pacing therapy in response to identifying the at least one suspect parameter prior to initiating action to handle the one or more indicated faults, and
determine whether a fault exists based on the at least one physiological response sensed during the delivery of pacing therapy in response to identifying the at least one suspect parameter, wherein, to identify at least one suspect parameter in the one or more monitored parameters indicative of one or more faults, the control module is further configured to execute one or more of analyzing clock speed, testing internal pacing circuitry, and testing discrete component leakage.

20. The device of claim 19, further comprising:
a housing;
a first electrode and a second electrode;
a first pacing output circuit located within the housing, wherein the first pacing output circuit is configured to deliver pacing therapy to the patient using the first electrode;
a second pacing output circuit located within the housing, wherein the second pacing output circuit is configured to deliver pacing therapy to the patient using the second electrode;
wherein the control module is coupled to the first pacing output circuit and the second pacing output circuit, wherein the control module is further configured to:
determine if a fault exists in the first pacing output circuit; and
reconfigure the second pacing output circuit to deliver pacing therapy using the first electrode if a fault is determined to exist in the first pacing output circuit.

21. The device of claim 20, wherein the control module is configured to:
configure the second pacing output circuit to deliver pacing therapy with the first electrode during a first time period; and
configure the second pacing output circuit to deliver pacing therapy with the second electrode during a second time period, wherein the first time period and the second time period do not overlap.

22. The device of claim 21, wherein the control module is further configured to set the voltage of the pacing therapy delivered by the second pacing output circuit to the higher of the voltage of the pacing therapy delivered with the first electrode using the first pacing output circuit and the voltage of the pacing therapy delivered with the second electrode using the second pacing output circuit.

23. The device of claim 20, wherein device further comprises a third electrode and a third pacing output circuit located in the housing, wherein the third pacing output circuit is configured to deliver pacing therapy to the patient using the third electrode,
wherein the control module is further configured to reconfigure the third pacing output circuit to deliver pacing therapy with at least one of the second electrode and the third electrode if a fault is determined to exist in the first pacing output circuit.

24. The device of claim 23, wherein the control module is further configured to:
configure the third pacing circuit to deliver pacing therapy with the second electrode during a first time period; and
configure the third pacing circuit to deliver pacing therapy with the third electrode during a second time period, wherein the first time period and the second time period do not overlap.

25. The device of claim 20, wherein, to determine if a fault exists in the first pacing output circuit, the control module is further configured to test the first pacing output circuit.

26. The device of claim 20, wherein the control module is further configured to reconfigure the first pacing output circuit to deliver pacing therapy with the second electrode if no fault is determined to exist in the first pacing output circuit.

27. The device of claim 20, wherein the first electrode is configured to deliver pacing therapy to the patient's right ventricle.

28. The device of claim 19, wherein, to sense at least one physiological response of the patient during the delivery of pacing therapy, the control module is further configured to sense, using the sensing apparatus, the at least one physiological response of the patient during the delivery of pacing therapy over a selected number of heart beats, and
wherein, to determine whether a fault exists, the control module is further configured to determine whether a fault exists based on the at least one physiological response sensed during the delivery of pacing therapy over the selected number of heart beats.

29. The device of claim 19, wherein, to determine whether a fault exists based on the at least one physiological response sensed during the delivery of pacing therapy, the control module is further configured to determine whether the at least one sensed physiological response is an expected physiological response in response to the delivery of pacing therapy.

30. The device of claim 19, wherein, to identify at least one suspect parameter in the one or more monitored parameters indicative of one or more faults, the control module is further configured to monitor at least one of delivered pacing capacitor energy and lead impedance.

31. The device of claim 19, wherein, to identify at least one suspect parameter in the one or more monitored parameters indicative of one or more faults, the control module is further configured to execute testing of a power supply.

32. An implantable medical device for use in delivering pacing therapy to a patient comprising:
  a therapy delivery module configured to deliver pacing therapy to a patient;
  sensing apparatus configured to monitor at least one physiological response of the patient in response to the delivery of pacing therapy; and
  a control module coupled to the therapy delivery module and to the sensing apparatus and configured to:
    initiate the delivery of pacing therapy to the patient,
    monitor one or more parameters of the implantable medical device during the delivery of pacing therapy,
    identify at least one suspect parameter in the one or more monitored parameters indicative of one or more faults associated with the implantable medical device that require action to be taken for handling of the one or more faults, wherein to identify at least one suspect parameter in the one or more monitored parameters indicative of one or more faults, the control module is further configured to execute one or more of analyzing clock speed, testing internal pacing circuitry, and testing discrete component leakage,
    sense, using the sensing apparatus, at least one physiological response of the patient during the delivery of pacing therapy in response to identifying the at least one suspect parameter prior to initiating action to handle the one or more indicated faults, and
    determine whether a fault exists based on the at least one physiological response sensed during the delivery of pacing therapy in response to identifying the at least one suspect parameter, wherein the device further comprises one or more leads, wherein the therapy delivery module comprises internal pacing circuitry coupled to the one or more leads and configured to deliver pacing therapy using the one or more leads,
    wherein the control module is further configured to execute diagnostics of the internal pacing circuitry and the one or more leads to determine if the detected fault is associated with one of the internal pacing circuitry and the one or more leads in response to determining that a fault exists.

33. An implantable medical device for use in delivering pacing therapy to a patient comprising:
  a therapy delivery module configured to deliver pacing therapy to a patient;
  sensing apparatus configured to monitor at least one physiological response of the patient in response to the delivery of pacing therapy; and
  a control module coupled to the therapy delivery module and to the sensing apparatus and configured to:
    initiate the delivery of pacing therapy to the patient,
    monitor one or more parameters of the implantable medical device during the delivery of pacing therapy,
    identify at least one suspect parameter in the one or more monitored parameters indicative of one or more faults associated with the implantable medical device that require action to be taken for handling of the one or more faults, wherein to identify at least one suspect parameter in the one or more monitored parameters indicative of one or more faults, the control module is further configured to execute one or more of analyzing clock speed, testing internal pacing circuitry, and testing discrete component leakage,
    sense, using the sensing apparatus, at least one physiological response of the patient during the delivery of pacing therapy in response to identifying the at least one suspect parameter prior to initiating action to handle the one or more indicated faults, and
    determine whether a fault exists based on the at least one physiological response sensed during the delivery of pacing therapy in response to identifying the at least one suspect parameter, wherein the control module is further configured to:
    modify the pacing therapy by changing at least one parameter of the pacing therapy in response to determining that a fault exists;
    sense, using the sensing apparatus, at least one physiological response of the patient during delivery of the modified pacing therapy; and
    perform fault handling operations if the at least one sensed physiological response of the patient during delivery of the modified pacing therapy is not an expected physiological response in response to the delivery of the modified pacing therapy.

34. An implantable medical device for use in delivering pacing therapy to a patient comprising:
  a therapy delivery module configured to deliver pacing therapy to a patient;
  sensing apparatus configured to monitor at least one physiological response of the patient in response to the delivery of pacing therapy; and
  a control module coupled to the therapy delivery module and to the sensing apparatus and configured to:
    initiate the delivery of pacing therapy to the patient,
    monitor one or more parameters of the implantable medical device during the delivery of pacing therapy,
    identify at least one suspect parameter in the one or more monitored parameters indicative of one or more faults associated with the implantable medical device that require action to be taken for handling of the one or more faults, wherein to identify at least one suspect parameter in the one or more monitored parameters indicative of one or more faults, the control module is further configured to execute one or more of analyzing clock speed, testing internal pacing circuitry, and testing discrete component leakage,
    sense, using the sensing apparatus, at least one physiological response of the patient during the delivery of pacing therapy in response to identifying the at least one suspect parameter prior to initiating action to handle the one or more indicated faults, and
    determine whether a fault exists based on the at least one physiological response sensed during the delivery of pacing therapy in response to identifying the at least one suspect parameter, wherein the control module is further configured to:
    modify the pacing therapy by changing at least one parameter of the pacing therapy in response to determining that a fault exists;
    sense, using the sensing apparatus, at least one physiological response of the patient during delivery of the modified pacing therapy; and
    perform fault handling operations if the at least one sensed physiological response of the patient during delivery of the modified pacing therapy is not an expected physiological response in response to the delivery of the modified pacing therapy, wherein, to change at least one parameter of the pacing therapy, the control module is further configured to change the pacing therapy to a maximum output for the pacing therapy.

35. An implantable medical device for use in delivering pacing therapy to a patient comprising:
a therapy delivery module configured to deliver pacing therapy to a patient;
sensing apparatus configured to monitor at least one physiological response of the patient in response to the delivery of pacing therapy; and
a control module coupled to the therapy delivery module and to the sensing apparatus and configured to:
initiate the delivery of pacing therapy to the patient,
monitor one or more parameters of the implantable medical device during the delivery of pacing therapy,
identify at least one suspect parameter in the one or more monitored parameters indicative of one or more faults associated with the implantable medical device that require action to be taken for handling of the one or more faults, wherein to identify at least one suspect parameter in the one or more monitored parameters indicative of one or more faults, the control module is further configured to execute one or more of analyzing clock speed, testing internal pacing circuitry, and testing discrete component leakage,
sense, using the sensing apparatus, at least one physiological response of the patient during the delivery of pacing therapy in response to identifying the at least one suspect parameter prior to initiating action to handle the one or more indicated faults, and
determine whether a fault exists based on the at least one physiological response sensed during the delivery of pacing therapy in response to identifying the at least one suspect parameter, wherein the control module is further configured to:
modify the pacing therapy by changing at least one parameter of the pacing therapy in response to determining that a fault exists;
sense, using the sensing apparatus, at least one physiological response of the patient during delivery of the modified pacing therapy; and
perform fault handling operations if the at least one sensed physiological response of the patient during delivery of the modified pacing therapy is not an expected physiological response in response to the delivery of the modified pacing therapy, wherein the control module is further configured to periodically sense, using the sensing apparatus, at a periodic sensing rate at least one physiological response of the patient during the delivery of pacing therapy for use in determining whether a fault exists, wherein the control module interrupts the periodic sensing when sensing at least one physiological response of the patient during the delivery of pacing therapy in response to identifying the at least one suspect parameter.

36. An implantable medical device for use in delivering pacing therapy to a patient comprising:
a therapy delivery module configured to deliver pacing therapy to a patient;
sensing apparatus configured to monitor at least one physiological response of the patient in response to the delivery of pacing therapy; and
a control module coupled to the therapy delivery module and to the sensing apparatus and configured to:
initiate the delivery of pacing therapy to the patient,
monitor one or more parameters of the implantable medical device during the delivery of pacing therapy,
identify at least one suspect parameter in the one or more monitored parameters indicative of one or more faults associated with the implantable medical device that require action to be taken for handling of the one or more faults, wherein to identify at least one suspect parameter in the one or more monitored parameters indicative of one or more faults, the control module is further configured to execute one or more of analyzing clock speed, testing internal pacing circuitry, and testing discrete component leakage,
sense, using the sensing apparatus, at least one physiological response of the patient during the delivery of pacing therapy in response to identifying the at least one suspect parameter prior to initiating action to handle the one or more indicated faults, and
determine whether a fault exists based on the at least one physiological response sensed during the delivery of pacing therapy in response to identifying the at least one suspect parameter, to handle a determined fault, the control module is further configured to reconfigure at least one of an electrode vector configuration according to a periodically-updated pacing reconfiguration table and pacing output circuit configuration for the pacing therapy in response to determining that a fault exists.

* * * * *